(12) United States Patent
Czerney et al.

(10) Patent No.: US 7,745,640 B2
(45) Date of Patent: Jun. 29, 2010

(54) HYDROPHILIC LABELS FOR BIOMOLECULES

(75) Inventors: Peter T. Czerney, Jena (DE); Wilhelm G. Frank, Jena (DE); Frank G. Lehmann, Jena (DE); Bernd G. Schweder, Jena (DE); Matthias S. Wenzel, Jena (DE)

(73) Assignee: Dyomics GmbH, Jena (DE)

( * ) Notice: Subject to any disclaimer, the term of this patent is extended or adjusted under 35 U.S.C. 154(b) by 292 days.

(21) Appl. No.: 11/566,699

(22) Filed: Dec. 5, 2006

(65) Prior Publication Data

US 2007/0128659 A1    Jun. 7, 2007

(30) Foreign Application Priority Data

Dec. 5, 2005  (DE) .................. 10 2005 058 587
Jun. 27, 2006 (DE) .................. 10 2006 029 454

(51) Int. Cl.
*C07D 209/02* (2006.01)
*A61K 31/40* (2006.01)

(52) U.S. Cl. ................... 548/455; 424/9.6; 514/414

(58) Field of Classification Search ............... 548/455; 424/9.6; 514/414
See application file for complete search history.

(56) References Cited

U.S. PATENT DOCUMENTS

| 5,268,486 | A |   | 12/1993 | Waggoner et al. |
| 5,627,027 | A |   | 5/1997 | Waggoner |
| 5,846,737 | A |   | 12/1998 | Kang |
| 6,083,485 | A | * | 7/2000 | Licha et al. ............ 424/9.6 |
| 6,967,251 | B2 |   | 11/2005 | Haugland et al. |
| 6,974,873 | B2 |   | 12/2005 | Leung et al. |
| 6,977,305 | B2 |   | 12/2005 | Leung et al. |
| 2006/0004188 | A1 |   | 1/2006 | Leung et al. |
| 2006/0099638 | A1 |   | 5/2006 | Leung et al. |
| 2007/0203343 | A1 | * | 8/2007 | West et al. ............ 548/148 |

FOREIGN PATENT DOCUMENTS

| DE | 4445065 A1 | 6/1996 |
| DE | 19717904 A1 | 10/1998 |
| DE | 19926460 A1 | 12/1999 |
| DE | 10046215 A1 | 4/2002 |
| DE | 10046215 B4 | 4/2002 |
| EP | 1181940 A2 | 2/2002 |
| EP | 1181940 B1 | 2/2002 |
| JP | 05-313304 | 11/1993 |
| WO | 2005/044923 A1 | 5/2005 |
| WO | 2005/103162 A1 | 11/2005 |

OTHER PUBLICATIONS

Search Report issued by the German Patent Office regarding App #10 2006 029 454.8 issued Oct. 10, 2006 (with English language summary).
Search Report issued by the German Patent Office regarding App #10 2006 057 345.5 issued May 21, 2007 (with English language summary).

* cited by examiner

*Primary Examiner*—Rebecca L Anderson
*Assistant Examiner*—Robert Havlin
(74) *Attorney, Agent, or Firm*—Thompson Hine LLP

(57) ABSTRACT

Compounds, compositions, and methods for optical, including fluorescence optical, determinations useful in labelling biomolecules such as protein and deoxyribonucleic acid for their detection and quantitation. The compounds are diastereomeric cyanines with high hydrophilicity and other desirable properties.

9 Claims, 12 Drawing Sheets

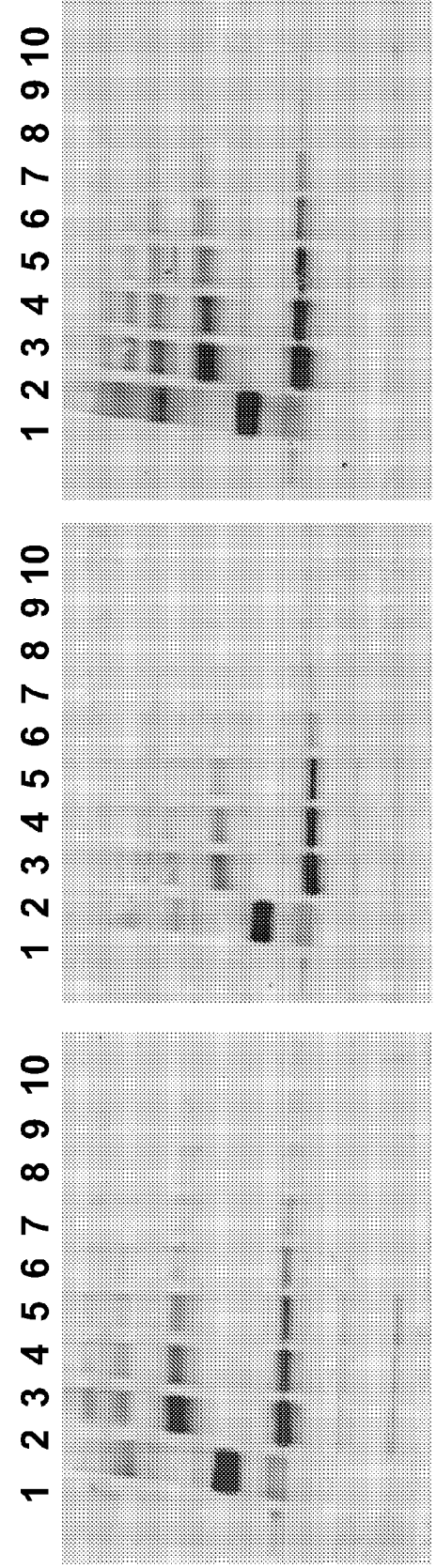

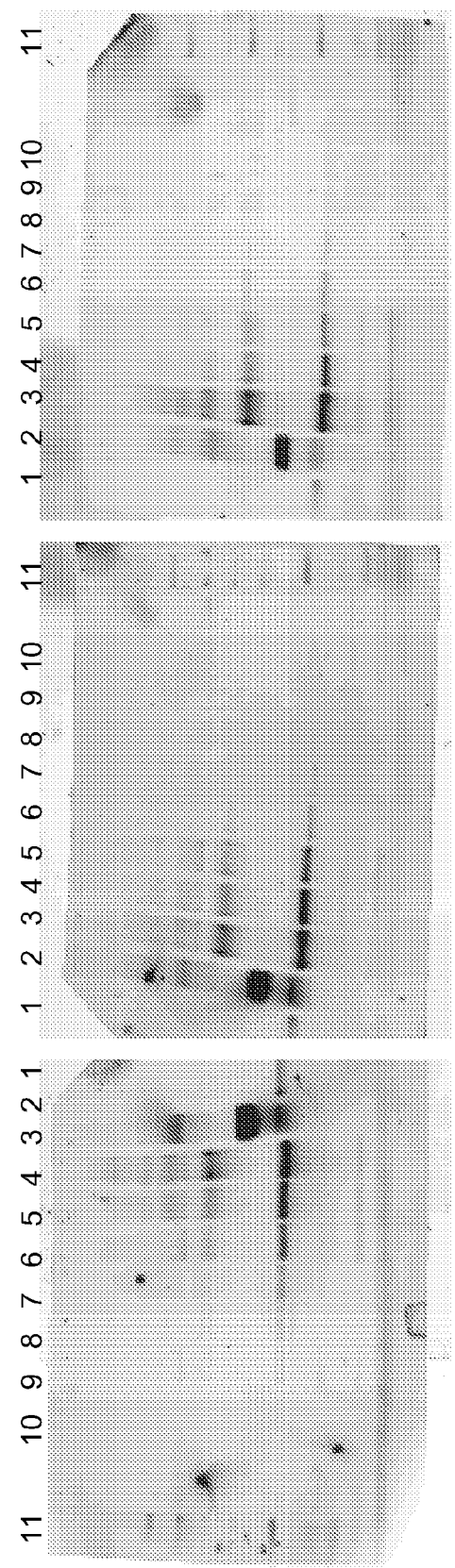

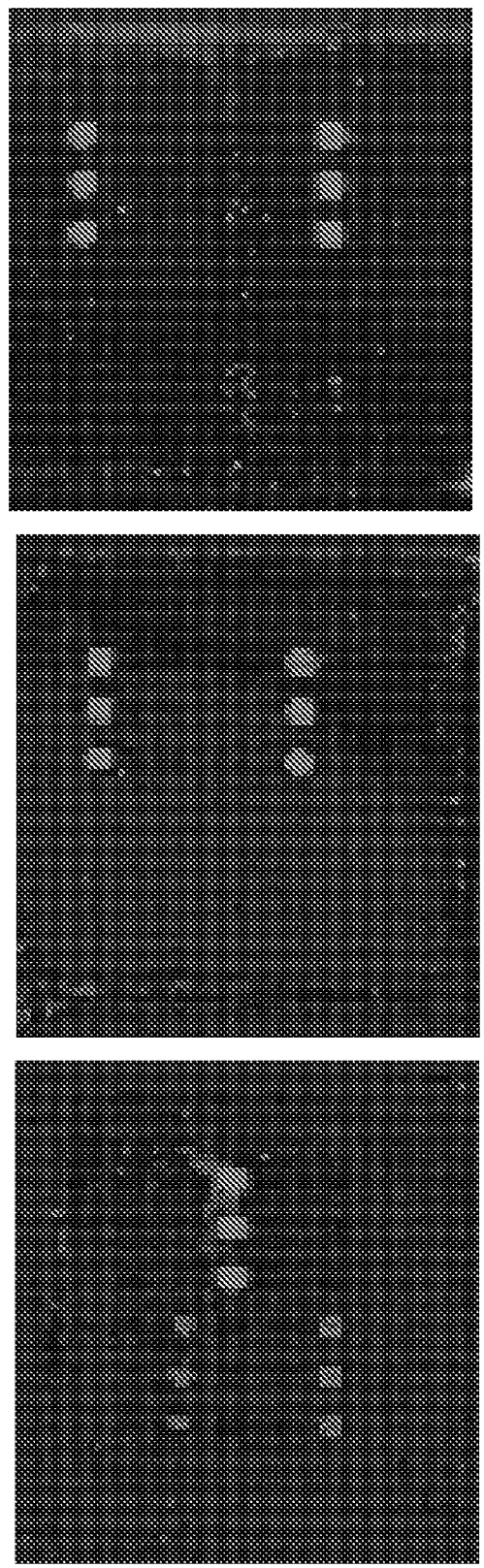

HYDROPHILIC LABELS FOR BIOMOLECULES

RELATED APPLICATIONS

This application claims priority from DE 10 2006 029 454.8 filed on Jun. 27, 2006, which claims priority from DE 10 2005 058 587.6 filed on Dec. 5, 2005.

TECHNICAL FIELD

Compounds and dye compositions and methods using the compounds for detecting and quantitating biomolecules such as proteins and DNA.

BACKGROUND

Compounds reactive with biomolecules such as antigens, antibodies, and/or DNA-segments with the corresponding complimentary species for measurements of enzyme kinetics, receptor-ligand interactions, nucleic acid hybridization kinetics in vitro as well as in vivo, etc. are useful. Such compounds are of interest for the pharmacological characterization of receptors and drugs, as well as other uses. For such applications, xanthylium salts (e.g., as disclosed in U.S. Pat. No. 5,846,737) or cyanines (e.g., as claimed in U.S. Pat. No. 5,627,027) had been used, but had the disadvantage of tending to aggregate and to form dimers, especially in aqueous solution, due to planarity of their π-system. Further, labels with insufficient hydrophilicity undergo non-specific interactions with various surfaces, which cause problems in purifying the corresponding conjugate and lead to an unsatisfactory signal to noise ratio.

Recent efforts have been directed to reduce the known disadvantages of cyanines by introducing additional substituents that increase the hydrophilicity of the compounds. Additional sulfonic acid functions have been introduced into the cyanine chromophore. For example, U.S. Pat. No. 6,083,485 (Licha) and U.S. patent application Ser. No. 09/968,401 and Ser. No. 09/989,853 (Molecular Probes) disclose cyanines in which one of the common methyl groups in the 3-position of the terminal indole heterocycle is substituted by an ω-carboxyalkyl function and in which the previously present (e.g. in Cy3 or Cy5) N-alkyl or N-ω-carboxyalkyl functions are replaced by N-ω-alkyl sulfonic acid functions. Published PCT Application No. WO 05/044923 discloses cyanines in which the common methyl substituent in the 3-position of the terminal indole heterocycle is substituted by a N-ω-alkyl sulfonic acid function. Cyanines with more than two sulfonic acid functions disclosed in these documents exhibited higher solubility and, in connection with this, lower tendency to dimer formation, in comparison to cyanines (Cy3, Cy5) described in U.S. Pat. No. 5,627,027.

Further improvements are desirable.

SUMMARY

Diastereomeric compounds, and dye compositions and methods using the compound, of the general formula I or formula II

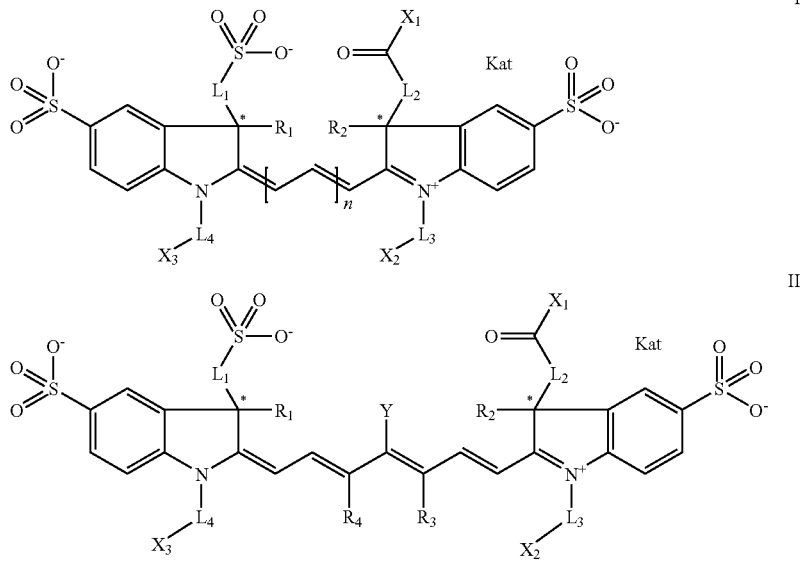

where formula I comprises

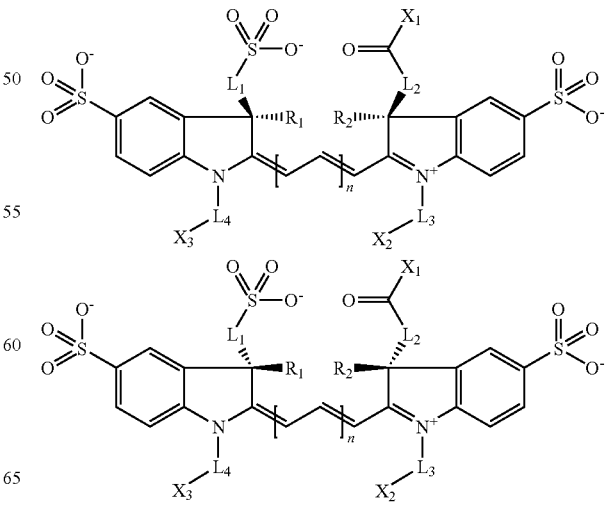

diastereomer Ia (mixture of two enantiomers) and
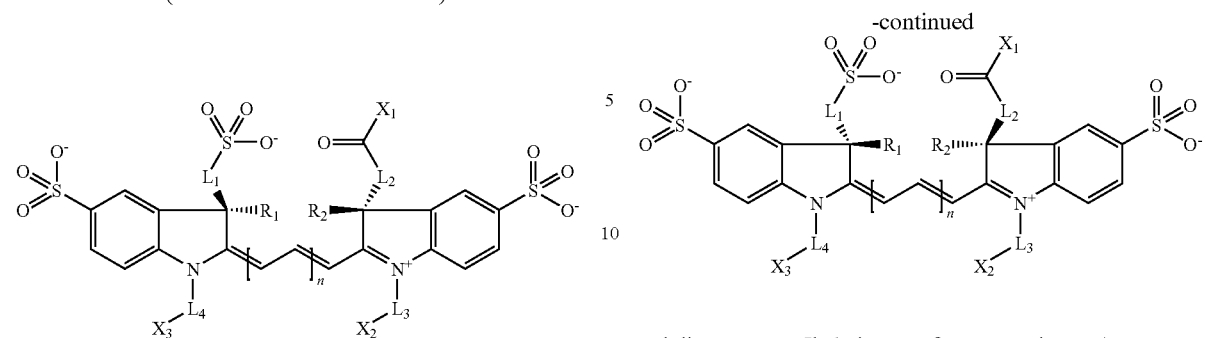
and diastereomer Ib (mixture of two enantiomers);
formula II comprises
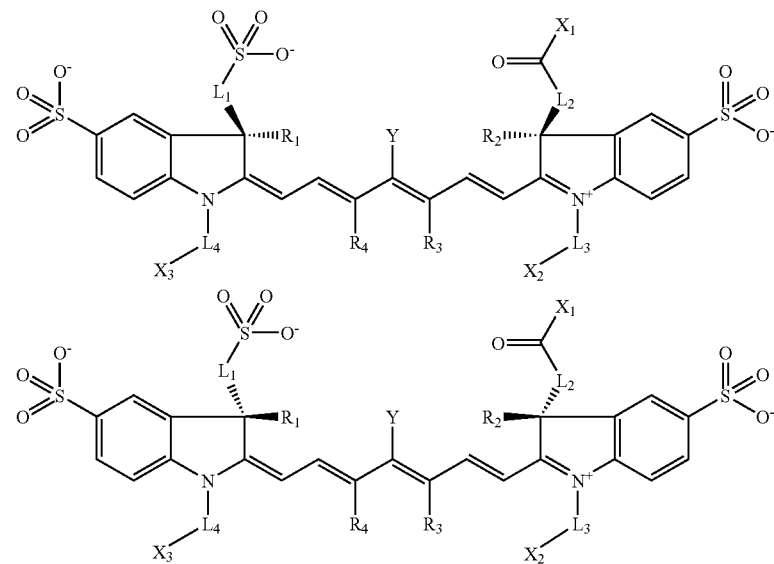
diastereomer IIa (mixture of two enantiomers) and
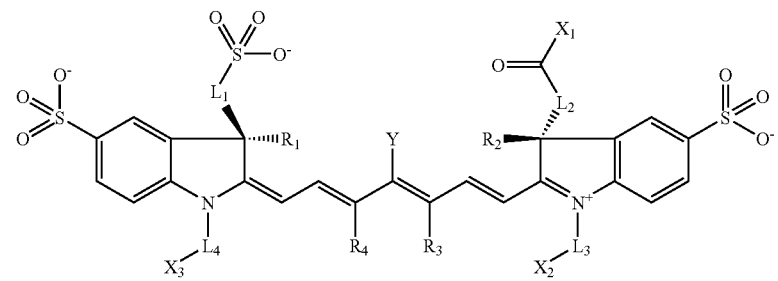

-continued

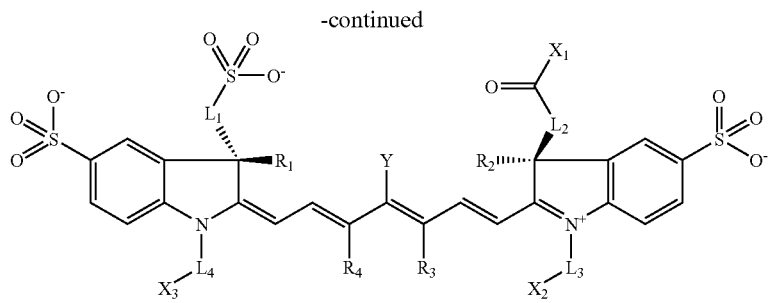

and diastereomer IIb (mixture of two enantiomers) or combinations thereof, whereby each diasteromer Ia, Ib, IIa, and IIb is a mixture of two enantiomers and whereby each of $R^1$ and $R^2$ is the same or different and is independently selected from the group consisting of an aliphatic and heteroaliphatic group;

each of $L_1$ to $L_4$ is the same or different and is independently selected from the group consisting of a divalent linear (—$(CH_2)_o$—, o=1 to 15), crossed, or cyclic alkylene group which can be substituted by at least one atom selected from the group consisting of oxygen, substituted nitrogen, and sulfur;

$X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5, 6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-$CO_2$—NHS, —NR-L-$CO_2$-STP, —NR-L-$CO_2$-TFP, —NR-L-CO-benzotriazole, —NR-L-CHO, —NR-L-maleimid, and —NR-L-NH—CO—$CH_2$—I, R is —H or is equal to $R^1$ or $R^2$ and L is equal to $L_1$ to $L_4$;

each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof;

Kat is a number of $Na^+$, $K^+$, $Ca^{2+}$, ammonia, or other cation(s) needed to compensate the negative charge brought by the cyanine;

n in formula I is a integer from 0 to 3;

Y in formula II is selected from the group consisting of fluorine, chlorine, bromine, a substituted phenoxy-, and a substituted arylmercapto-(phenyl sulfanyl-) function; and each of $R^3$ and $R^4$ in formula II is the same or different and is independently an aliphatic or heteroaliphatic group respectively, or forms together the divalent structural element selected from the group consisting of —$(CH_2)_m$—, —$(CH_2)_m$O$(CH_2)_{m'}$—, —$(CH_2)_mS(CH_2)_{m'}$—, —$(CH_2)_m$CH=CH—, and —OCH=CH— where each of m and m' is the same or different and is a integer from 2 to 6.

The following drawings, description, and examples further illustrate embodiments of the invention.

BRIEF DESCRIPTION OF THE DRAWINGS

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

FIGS. 1A, 1B, and 1C show Western blots probed with one compound (formula OB-3a) conjugated to different secondary detection reagents.

FIGS. 2A, 2B, and 2C show Western blots probed with another compound (formula OB-5a) conjugated to different secondary detection reagents.

FIGS. 4A, 4B, and 4C show microarrays probed with another compound (formula OB-5a) conjugated to different secondary detection reagents.

FIG. 10 shows rabbit immunoglobulin coated microwell plates detected with conjugates of compound formula OB-5a.

DETAILED DESCRIPTION

Figure 3A:
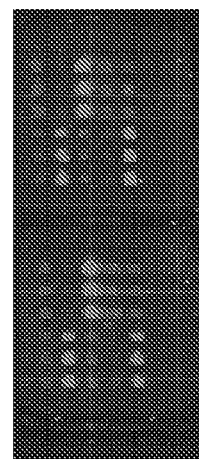
FIGS. 3A, 3B, and 3C show microarrays probed with one compound (formula OB-3a) conjugated to different secondary detection reagents.

Diastereomeric cyanine compounds are disclosed that are useful as labels in optical, especially fluorescence optical, determination and detection methods. The compounds, also referred to herein as dyes and/or labels, have very high hydrophilicity, high molar absorbance, high photo-stability, and high storage stability. These compounds can be excited by monochromatic (e.g., lasers, laser diodes) or polychromatic (e.g., white light sources) light in the ultraviolet (UV), visible, and near infrared (NIR) spectral region to generate emission of fluorescence light.

Typical application methods are based on the reaction of the compounds with biomolecules such as proteins (e.g., antigens, antibodies, etc.), DNA and/or RNA segments, etc. with the corresponding complimentary species. Thus, among other embodiments, measurements of enzyme kinetics, receptor-ligand interactions, and nucleic acid hybridization kinetics in vitro as well as in vivo are enabled. Furthermore, the compounds are of interest for the pharmacological characterization of receptors and drugs. Applications include but are not limited to uses in medicine, pharmacy, biological sciences, materials sciences, environmental control, detection of organic and inorganic micro samples occurring in nature, etc.

The application discloses use of cyanines in which one terminal heterocycle has, in 3-position, a solubilizing or ionizing group (e.g. ω-alkyl sulfonic acid function) and in which the other terminal heterocycle has a function for the coupling to biomolecules (e.g. a ω-carboxyalkyl function). These cyanines exhibit a chiral C-atom in each 3-position through derivatizing both terminal indole heterocycles in 3-position, once with a ω-alkyl sulfonic acid function and once with a ω-carboxyalkyl function, resulting in a mixture of diastereomers.

The disclosed diastereomeric cyanines have observable further minimized aggregation between the dye molecules, due to the different spatial arrangement of the substituents. Precipitation of cyanine-protein conjugates with a high cyanine-protein ratio from aqueous solution is minimized or prevented. This is due to the substitution pattern, combined with the strong hydrophilicity of these cyanines (at least three sulfonic acid residues). Undesired nonspecific interactions are reduced, compared to other cyanines.

These specially substituted and strongly hydrophilic compounds, based on diastereomeric cyanines of the general formulas I and II

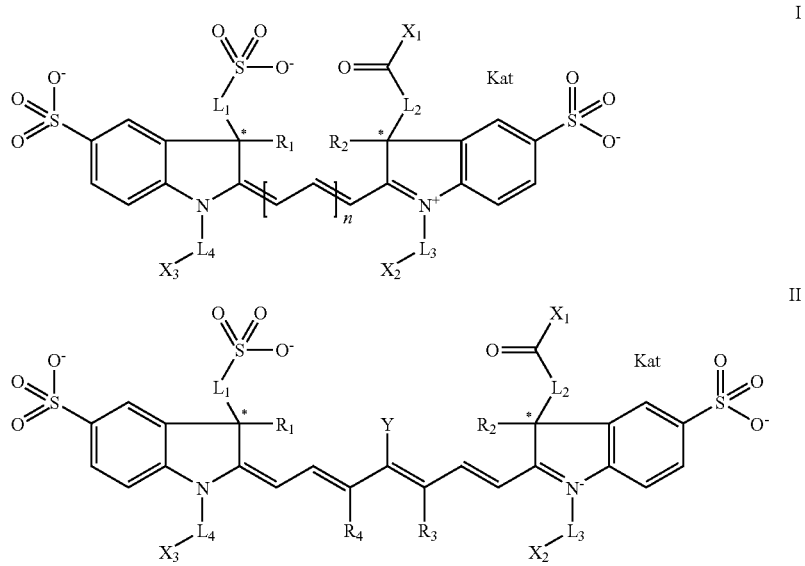

are disclosed. The mixture of the diastereoisomers I and II was able to be separated, as demonstrated in the following example of the general formula I, and the isolated diastereoisomers (i.e., Ia and Ib or IIa and IIb) was used for optical detection methods.

Formula I contains

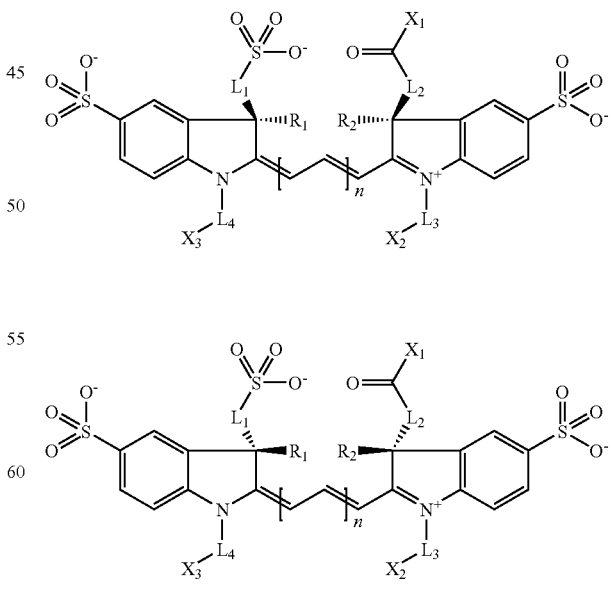

diastereomer Ia (mixture of two enantiomers) and

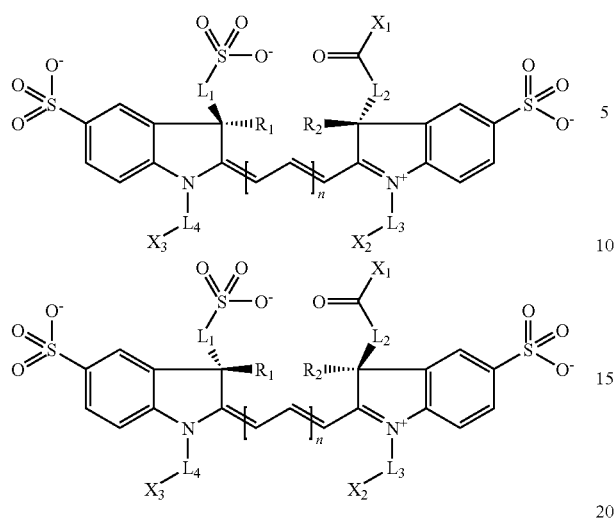
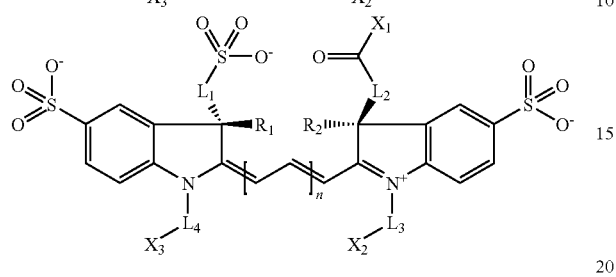
and diastereomer Ib (mixture of two enantiomers);
formula II contains
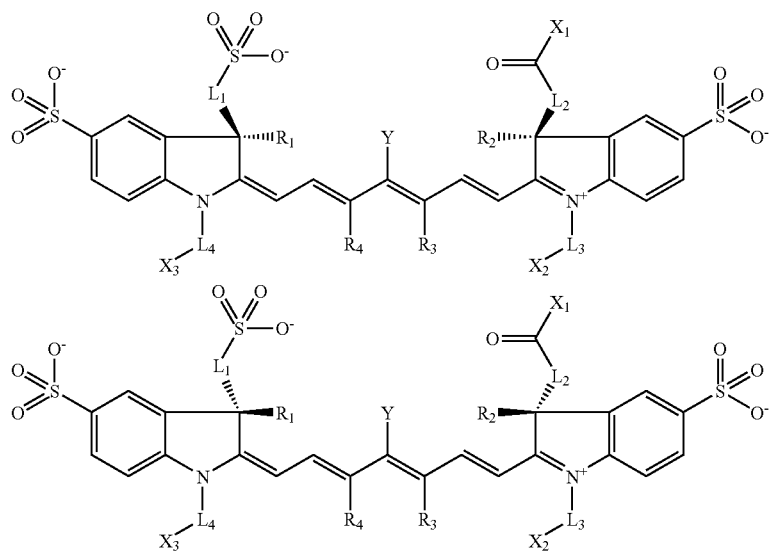
diastereomer IIa (mixture of two enantiomers) and
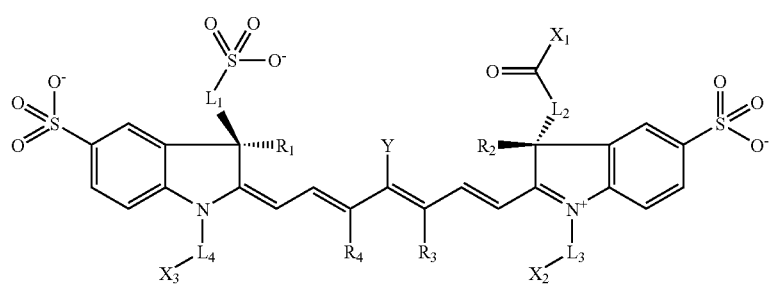

-continued

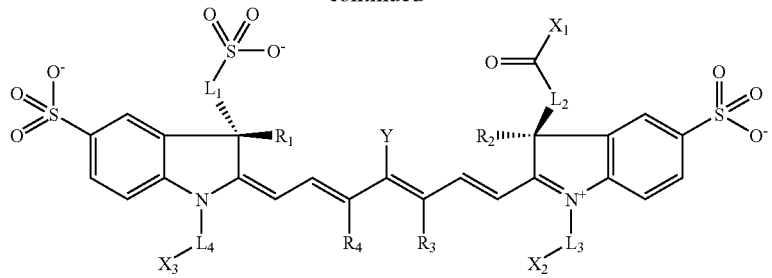

and diastereomer IIb (mixture of two enantiomers) or combinations thereof.

Each diastereomer Ia, Ib, IIa, and IIb is a mixture of two enantiomers. In each of these structures, $R^1$ and $R^2$ is the same or different and is independently selected from the group consisting of an aliphatic or heteroaliphatic group; each of $L_1$ to $L_4$ is the same or different and is independently selected from the group consisting of a divalent linear (—$(CH_2)_o$—, o=1 to 15), crossed, or cyclic alkylene group which can be substituted by at least one atom selected from the group consisting of oxygen, substituted nitrogen, and sulfur; $X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, or —NR-L-OH, —NR-L-O-phosphoramidite, —NR-L-SH, —NR-L-$NH_2$, —NR-L-NH—$NH_2$, —NR-L-$CO_2$H, —NR-L-$CO_2$—NHS, —NR-L-$CO_2$-STP, —NR-L-$CO_2$-TFP, —NR-L-CO-benzotriazole, —NR-L-CHO, —NR-L-maleimid, or —NR-L-NH—CO—$CH_2$—I and R is —H or is equal to $R^1$ or $R^2$ and L is equal to $L_1$ to $L_4$; each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof; Kat represents a certain number of $Na^+$, $K^+$, $Ca^{2+}$, ammonia, or other cation(s) needed to compensate the negative charge brought by the cyanine; n in formula I is a integer from 0 to 3; Y in formula II is selected from the group consisting of fluorine, chlorine, bromine, a substituted phenoxy-, a substituted arylmercapto-(phenyl sulfanyl-) function; and each of $R^3$ and $R^4$ in formula II is independently the same or different and is an aliphatic (e.g., $CH_3$) or heteroaliphatic group respectively, or forms together the divalent structural element selected from the group consisting of —$(CH_2)_m$—, —$(CH_2)_mO(CH_2)_{m'}$—, —$(CH_2)_mS(CH_2)_{m'}$—, —$(CH_2)_m$CH=CH—, and —OCH=CH— where each of m and m' is the same or different and is independently an integer from 2 to 6.

The disclosed compounds can be used as chromophores and/or fluorophores. For example, they can be used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc.

Covalent coupling of the compounds occur via the ω-carboxyalkyl function positioned at the 3-position of the indole ring. This function can be activated by protein chemistry methods known to one skilled in the art, e.g., as NHS-ester, acid fluoride, TFP- or STP-ester, and which is reacted with the amino function of the biomolecule under formation of amide of an acid. The coupling reaction may be performed in organic or aqueous solutions between pH 5 and pH 12. The compound need not be dissolved in an organic solvent, such as dimethyl formamide (DMF) or dimethyl sulfoxide (DMSO) prior to adding the sample to be evaluated. In one embodiment, the coupling reaction may be performed in a 100% aqueous solution. In one embodiment, the coupling reaction may be performed at room temperature (about 20° C. to about 22° C.).

The resulting compound and biomolecule conjugates exhibit fluorescent properties. They may be used in optical, including fluorescence optical, qualitative and quantitative determination methods. Examples of such methods include, but are not limited to, immunotests, hybridization methods, chromatographic and electrophoretic methods, fluorescence resonance energy transfer (FRET) systems, high throughput screenings, analysis of receptor-ligand interactions on a microarray, etc.

Compounds of the general formulas I and/or II and any of the embodiments can be used as dyes for optical labelling of organic or inorganic biomolecules, also referred to as recognition units. Recognition units are molecules having specificity and/or affinity for a specific group of molecules. Examples of recognition units include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein A/G and Protein L, sequences of amino acids or metals that have affinity for each other (e.g., histidine sequences bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormone), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. Ionic interactions are established between these recognition units and compounds (formulas I and/or II), resulting in labelling. The recognition unit and compound can be covalently connected. The result is a conjugate for qualitative or quantitative determination of various biomaterials or other organic or inorganic materials using optical methods.

Compounds of the general formulas I and/or II and any of the embodiments, as well as systems derived therefrom, can be used in optical, including fluorescence optical, qualitative and quantitative determination methods to diagnose properties of cells (molecular imaging), in biosensors (point of care measurements), for investigation of the genome, and in miniaturizing technologies. Cytometry, cell sorting, fluorescence correlation spectroscopy (FCS), ultra high throughput screening (uHTS), multicolour fluorescence in situ hybridisation (mc-FISH), FRET-systems and microarrays (DNA- and protein chips) belong to typical application fields.

A microarray is a grid-like arrangement of molecules immobilized on at least one surface. The microarray can be used to study receptor ligand interactions. A grid-like arrangement means more than two molecules different from each other that are located within an area and in different predefined regions with known position.

A receptor is a molecule that exhibits an affinity to a given ligand. Receptors can be naturally occurring or artificially made molecules. Receptors can be used in their pure form or bound to another specie. Receptors can be coupled covalently or noncovalently to a binding partner either directly or through a coupling mediator. Examples for receptors include but are not limited to agonists and antagonists for cell membrane receptors, toxins and other poisons, viral epitopes, hormone like opiates and steroids, hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. A ligand is a molecule that is recognized by a certain receptor. Examples for ligands include but are not limited to agonists and antagonists for cell membrane receptors, toxins and other poisons, viral epitopes, hormones like opiates and steroids, hormone receptors, peptides, enzymes, enzyme substrates, drugs acting as cofactors, lectins, sugars, oligonucleotides, nucleic acids, oligosaccharides, proteins, antibodies, etc.

In one embodiment, the compounds of formulas I and II are synthesized by condensing the two differently substituted CH-acidic indole heterocycles and a C-1, C-3, or C-5 building block. Additional methods for synthesis may be used. One example involves condensing one of the CH-acidic indole heterocycles in a first reaction step with the C-1, C-3, or C-5 building block, followed by isolating the 1:1 condensation product which is reacted subsequently with the second CH-acidic indole heterocycle through condensation to the cyanine. The sequence of use of the CH-acidic indole heterocycles is thereby irrelevant. Thus a plurality of differently functionalized, strongly hydrophilic, diastereomeric compounds which differ in total charge and specifity/reactivity of the active groups used for their immobilization can be easily prepared.

The disclosed compounds modified with reactive groups that include, but are not limited to, iodoacetyl, maleimide, hydrazides, N-hydroxysuccinimides, sulfonyl chloride, phenylazides, as known to one skilled in the art, may be used to label macromolecules (e.g., antibodies, streptavidin, etc) using methods known to one skilled in the art. For example, streptavidin, reconstituted or dialyzed against sodium borate or sodium carbonate buffer, between pH 8.5 to pH 9.0, may be reacted with a 5-10 molar excess of N-hydroxysuccinimide activated cyanine dye that is sulfonated and free of hydrophobic groups. The reaction is carried out for one to two hours at room temperature (about 20° C. to about 22° C.) and then dialyzed against several changes of phosphate buffered saline (pH 7.2). The resulting dye-macromolecule conjugates may be used in applications such as in detection of specific proteins in immunoassays, sugars in glycoproteins with lectins, protein-protein interactions, oligonucleotides in nucleic acid, hybridization, and in Electrophoretic Mobility Shift Assays (EMSA).

The following examples further describe and enable the inventive compounds and methods.

Example 1

Synthesis of Compounds of the General Formula I

1. Synthesis of 1-ethyl-3-methyl-2-((E)-2-phenylamino-vinyl)-5-sulfo-3-(3-sulfo-propyl)-3H-indolium sodium salt 0.794 g (2 mmol) 3-(3-sulfopropyl)-2,3-dimethyl-5-sulfonato-1-ethyl-3H-indolium sodium salt and 0.49 g (2.5 mmol) N,N'-diphenyl-formamidine were dissolved in 20 ml methanol and stirred for about four hours under reflux. The solvent mixture was removed in vacuum after cooling to room temperature. The residue was washed carefully with ethyl acetate. A dark yellow solid was obtained which was processed without further purification.

2. Synthesis of 2-{(E)-3-[3-(3-carboxy-propyl)-3-methyl-5-sulfo-1-(3-sulfo-propyl)-1,3-dihydro-indol-(2E)-ylidene]-propenyl}-1-ethyl-3-methyl-5-sulfo-3-(3-sulfo-propyl)-3H-indolium trisodium salt (OB-3)

500 mg (1 mmol) 1-ethyl-3-methyl-2-((E)-2-phenylamino-vinyl)-5-sulfo-3-(3-sulfo-propyl)-3H-indolium trisodium salt and 483 mg (1 mmol) 3-(3-carboxypropyl)-2,3-dimethyl-5-sulfonato-1-(3-sulfopropyl)-3H-indolium
sodium salt were dissolved in a mixture of 10 ml acetic acid and 10 ml acetic anhydride. Subsequently, 5 ml pyridine was added. The solution was stirred under reflux for fifteen minutes.

Twenty ml ether was added after cooling to room temperature. The obtained precipitate, which was a mixture of the diastereoisomers OB-3a and OB-3b, was extracted by suction, washed with ether, and dried.

The residue was purified by column chromatography: RP-18: acetonitrile/water, 2/8+1% conc. HCl; the diastereomeres were separated from each other thereby. The fractions containing the pure compounds OB-3a or OB-3b were united whereby the diastereomers were kept separated, followed by neutralization with NaHCO$_3$ and evaporation. Purification of the single diastereomeric compound was completed via a RP-18 column, acetonitrile/water, 2/8 without acid.

The corresponding fractions were united again and the solvent was removed by distillation. The two products (diastereomers OB-3a and OB-3b) were dried in high vacuum. The yield was about 15 percent per diastereomer.

Diastereomer OB-3a:

UV-vis (ethanol): $\lambda_{max}$=560 nm

MS (ES,−) [M/z]: 271.8 [M]$^{3-}$

Diastereomer OB-3b:

UV-vis (ethanol): $\lambda_{max}$=562 nm

MS (ES,−) [M/z]: 419.1 [M+Na]$^{2-}$; 271.8 [M]$^{3-}$

3. Synthesis of 1-ethyl-3-methyl-2-((1E,3E)-4-phenylamino-buta-1,3-dienyl)-5-sulfo-3-(3-sulfo-propyl)-3H-indolium sodium salt 0.794 g (2 mmol) 3-(3-sulfopropyl)-2,3-dimethyl-5-sulfonato-1-ethyl-3H-indolium sodium salt and 0.65 g malonaldehyde-bisphenylimin-hydrochloride were dissolved in a mixture of 10 ml acetic acid and 10 ml acetic anhydride and stirred at 120° C. for four hours. The solvent mixture was removed by distillation in vacuum after cooling to room temperature. The residue was washed with ethyl acetate. A dark brown solid was obtained which was processed without further purification.

4. Synthesis of 2-{(1E,3E)-5-[3-(3-carboxy-propyl)-3-methyl-5-sulfo-1-(3-sulfo-propyl)-1,3-dihydro-indole-(2E)-ylidene]-penta-1,3-dienyl}-1-ethyl-3-methyl-5-sulfo-3-(3-sulfo-propyl)-3H-indolium trisodium salt (OB-5)

516 mg (1 mmol) 1-ethyl-3-methyl-2-((1E,3E)-4-phenylamino-buta-1,3-dienyl)-5-sulfo-3-(3-sulfo-propyl)-3H-indolium sodium salt and 483 mg (1 mmol) 3-(3-carboxypropyl)-2,3-dimethyl-5-sulfonato-1-(3-sulfopropyl)-3H-indolium sodium salt were dissolved in a mixture of 10 ml acetic acid and 10 ml acetic anhydride followed by the addition of 5 ml pyridine. The solution was stirred under reflux for 15 min. Twenty ml ether was added after cooling to room temperature. The obtained precipitate (mixture of the diastereomers OB-5a and OB-5b) was extracted by suction, washed with ether, and dried.

The residue was purified by column chromatography: RP-18 acetonitrile/water, 2/8+1% conc. HCl; the diastereomers were separated from each other thereby. The fractions containing the pure diastereomers OB-5a or OB-5b were united whereby the diastereomeres were kept separated, followed by neutralization and evaporation. Purification of the single diastereomeric compound was completed via a RP-18 column, acetonitrile/water, 2/8 without acid.

The corresponding fractions were united and the solvent was removed by distillation. The two products (diastereomers OB-5a and OB-5b) were dried in high vacuum.

The yield was about 15 percent per diastereomer.

Diastereomere OB-5a:

UV-vis (ethanol): $\lambda_{max}$=655 nm

MS (ES,−) [M/z]: 432.2 [M+Na]$^{2-}$; 280.5 [M]$^{3-}$

Diastereomere OB-5b:

UV-vis (ethanol): $\lambda_{max}$=654 nm

MS (ES,−) [M/z]: 432.1 [M+Na]$^{2-}$; 280.5 [M]$^{3-}$

5. Synthesis of 3-methyl-2-((1E,3E)-4-phenylamino-buta-1,3-dienyl)-5-sulfo-1,3-bis-(3-sulfo-propyl)-3H-indolium disodium salt 1.03 g (2 mmol) 1,3-bis-(3-sulfopropyl)-2,3-dimethyl-5-sulfonato-3H-indolium disodium salt and 0.65 g (2.5 mmol) malonaldehyde-bisphenylimin-hydrochloride were dissolved in a mixture of 10 ml acetic acid and 10 ml acetic anhydride and stirred at 120° C. for about four hours. The solvent mixture was removed in vacuum after cooling to room temperature. The residue was washed with ethyl acetate. A dark brown solid was obtained which was processed without further purification.

6. Synthesis of 2-{(1E,3E)-5-[3-(3-carboxy-propyl)-3-methyl-5-sulfo-1-(3-sulfo-propyl)-1,3-dihydro-indole-(2E)-ylidene]-penta-1,3-dienyl}-3-methyl-5-sulfo-1,3-bis-(3-sulfo-propyl)-3 H-indolium tetrasodium salt (OB-5.5)

642 mg (1 mmol) 3-methyl-2-((1E,3E)-4-phenylamino-buta-1,3-dienyl)-5-sulfo-1,3-bis-(3-sulfo-propyl)-3H-indolium disodium salt and 483 mg (1 mmol) 3-(3-Carboxypropyl)-2,3-dimethyl-5-sulfonato-1-(3-sulfopropyl)-3H-indolium sodium salt were dissolved in a mixture of 10 ml acetic acid and 10 ml acetic anhydride. Five ml pyridine was added. The solution was stirred under reflux for 15 min. Twenty ml ether was added after cooling to room temperature. The obtained precipitate (mixture of the diastereomers OB-5.5a and OB-5.5b) was extracted by suction, washed with ether, and dried.

The residue was purified by column chromatography: RP-18: acetonitrile/water, 2/8+1% conc. HCl; the diastereomeres were separated from each other thereby. The fractions containing the pure diastereomer OB-5.5a or OB-5.5b were united whereby the diastereomers were kept separated, followed by neutralization with NaHCO₃ and evaporation. Purification of the single diasteromeric compound was completed via a RP-18 column, acetonitrile/water, 2/8 without acid.

The corresponding fractions were united and the solvent was removed by distillation. The two products (diastereomers OB-5.5a and OB-5.5b) wee dried in high vacuum. The yield was about 10 percent per diastereomer.

Diastereomer OB-5.5a:

UV-vis(Ethanol): $\lambda_{max}$=654 nm

MS (ES,−) [M/z]: 490.2 [M+2Na]$^{2-}$; 319.4 [M+Na]$^{3-}$; 233.6 [M]$^{4-}$

Diastereomer OB-5.5b:

UV-vis(Ethanol): $\lambda_{max}$=655 nm

MS (ES,−) [M/z]: 490.2 [M+2Na]$^{2-}$; 319.3 [M+Na]$^{3-}$; 233.5 [M]$^{4-}$

7. Synthesis of 2-{(1E,3E,5E)-7-[3-(3-Carboxy-propyl)-3-methyl-5-sulfo-1-(3-sulfo-propyl)-1,3-dihydro-indol-(2E)-ylidene]-hepta-1,3,5-trienyl}-1-ethyl-3-methyl-5-sulfo-3-(3-sulfo-propyl)-3H-indolium trisodium salt (OB-7)

397 mg (1 mmol) 3-(3-sulfopropyl)-2,3-dimethyl-5-sulfonato-1-ethyl-3H-indolium sodium salt and 284 mg (1 mmol) phenyl-[(2E,4E)-5-phenylamino-penta-2,4-dien-(E)-ylidene]-ammonium chloride were dissolved in 10 ml acetic acid and 10 ml acetic anhydride and stirred at 120° C. for one hour. 483 mg (1 mmol) 3-(3-carboxypropyl)-2,3-dimethyl-5-sulfonato-1-(3-sulfopropyl)-3H-indolium sodium salt and 5 ml pyridine were added. The mixture was stirred at 170° C. for twenty min. Twenty ml ether was added after cooling to room temperature. The obtained precipitate (mixture of the diastereomers OB-7a and OB-7b) was extracted by suction, washed with ether, and dried.

The residue was purified by column chromatography: RP-18: acetonitrile/water, 2/8+1% conc. HCl. The diastereomers were separated from each other thereby. The fractions containing the pure diasteromer OB-7a or OB-7b were united whereby the diastereomers were kept separated, followed by neutralization with NaHCO₃ and evaporation. Purification of the single diastereomeric compound was completed via a RP-18 column, acetonitrile/water, 2/8 without acid.

The corresponding fractions were united and the solvent was removed by distillation. The two products (diastereomers OB-7a and OB-7b) were dried in high vacuum. The yield was about 2 percent per diastereomer.

Diastereomer OB-7a:

UV-vis (ethanol): $\lambda_{max}$=752 nm

MS (ES,−) [M/z]: 445.1 [M+Na]$^{2-}$; 289.2 [M]$^{3-}$

Diastereomer OB-7b:

UV-vis (ethanol): $\lambda_{max}$=751 nm

MS (ES,−) [M/z]: 445.1 [M+Na]$^{2-}$; 289.2 [M]$^{3-}$

Example 2

Compounds of the General Formula II 8.2-((E)-2-{3-[2-[3-(3-carboxy-propyl)-3-methyl-5-sulfo-1-(3-sulfo-propyl)-1,3-dihydro-indol-(2E)-ylidene]-eth-(E)-ylidene]-2-chloro-cyclohexyl}-vinyl)-1-ethyl-3-methyl-5-sulfo-3-(3-sulfo-propyl)-3H-indolium trisodium salt (OB-8)

397 mg (1 mmol) 3-(3-sulfopropyl)-2,3-dimethyl-5-sulfonato-1-ethyl-3H-indolium sodium salt and 358 mg (1 mmol) [1-{2-chloro-3-[1-phenylamino-meth-(E)-ylidene]-cyclohex-1-enyl}-meth-(E)-ylidene]-phenyl-ammonium-chloride were dissolved in 10 ml acetic acid and 10 ml acetic anhydride and stirred at 120° C. for one hour. 483 mg (1 mmol) 3-(3-carboxypropyl)-2,3-dimethyl-5-sulfonato-1-(3-sulfopropyl)-3H-indolium and 5 ml pyridine were then added. The mixture was stirred at 170° C. for about twenty min. The obtained precipitate (mixture of the diastereoisomers OB-8a and OB-8b) was extracted by suction, washed with ether, and dried.

The residue was purified by column chromatography: RP-18: acetonitrile/water, 2/8+1% conc. HCl. The diastereomeres were separated from each other thereby. The fractions containing the pure diastereosomer OB-8a or OB-8b were united whereby the diasteromers were kept separated, followed by neutralization with NaHCO$_3$ and evaporation. Purification of the single diasteromeric compound was repeated via a RP-18 column, acetonitrile/water, 2/8 without acid.

The corresponding fractions were united and the solvent was removed by distillation. The two products (diastereomer OB-8a and OB-8b) were dried in high vacuum. The yield was about 1 percent per diastereomer.

Diastereomer OB-8a:

UV-vis (ethanol): $\lambda_{max}$=784 nm

MS (ES,−) [M/z]: 482.1 [M+Na]$^{2-}$; 313.7 [M]$^{3-}$

Diastereomer OB-8b:

UV-vis (ethanol): $\lambda_{max}$=784 nm

MS (ES,−) [M/z]: 482.2 [M+Na]$^{2-}$; 313.7 [M]$^{3-}$

Example 3

General Synthesis of N-Hydroxysuccinimidyl Esters ($X_1$=—NHS)

20 μmol dye of the pure diasteromeric compound of type Ia, Ib, IIa, or IIb with $X_1$=—OH, 8 mg (40 μmol) dicyclohexylcarbodiimide, and 5 mg (40 μmol) N-hydroxysuccinimide were dissolved in 2 ml of DMF and 100 μl water. Six μl (40 μmol) triethylamine was then added. The reaction mixture was stirred at room temperature (about 20° C. to about 22° C.) for 24 hours and then filtered. The solvent was removed and the residue was washed with diethylether. The reaction proceeded quantitatively.

Example 4

General Synthesis of Maleimides ($X_1$=—NH—CH$_2$CH$_2$-Maleimid)

20 μmol N-Hydroxysuccinimid-Ester of the pure diastereomeric compound of type Ia, Ib, IIa, or IIb with $X_1$=—NHS were dissolved in 2 ml DMF and 100 μl water and mixed with 7.6 mg (30 μmol) 2-Maleimidoethylamine-trifluoracetate and 5 μl (30 μmol) N-Ethyldiisopropyl-amine. The reaction mixture was stirred for three hours at room temperature (about 20° C. to about 22° C.). The solvent was evaporated under reduced pressure. The residue was washed with diethylether and acetone and dried in vacuum. The reaction proceeded quantitatively.

Example 5

General Synthesis of Iodoacetamides ($X_1$=—NH—CH$_2$CH$_2$—NH—CO—CH$_2$—I)

20 μmol N-Hydroxysuccinimid-Ester of the pure Diastereomeric compound of type Ia, Ib, IIa, or IIb with $X_1$=—NHS were dissolved in 2 ml DMF and 100 μl water, followed by the addition of 40 mg (300 μmol) Ethylendiamindihydrochlorid and 26 μl (150 μmol) N-Ethyldiisopropyl-amine. The reaction mixture was stirred for three hours at room temperature (about 20° C. to about 22° C.). The solvent was then evaporated under reduced pressure, the residue was dissolved in methanol, and the ethylendiamindihydrochlorid was removed by filtration. The methanol was evaporated under reduced pressure.

The residue was dissolved in 2 ml dry DMF, followed by then addition of 7 mg (25 μmol) N-Succinimidyl iodoacetate and 4 μl (25 μmol) N-ethyldiisopropylamine. The reaction mixture was stirred for three hours at room temperature. The solvent was evaporated under reduced pressure and the residue was purified via reverse phase HPLC.

Example 6

Conjugation to Proteins

Compounds that are rendered reactive may be conjugated to macromolecules, such as protein (e.g., antibodies, Streptavidin) and used in immunofluorescence assays (e.g. Western blot, ELISA, flow cytometry, in-cell assays, etc. Reactive dyes conjugated to oligonucleotides may be used in hybridization assays, Northern blots, Southern blots, etc.

Ten mg goat anti-rabbit IgG (H+L) (GAR) and 10 mg goat anti-mouse IgG (H+L) (GAM) at 10 mg/ml were dialyzed overnight against 5 L 50 mM borate buffer, pH 8.4. Each of the dialyzed antibodies were labeled with 10 molar excess of the pure diasteromeric compound formula OB-3a with $X_1$=—NHS that had been reconstituted in 0.1 ml MilliQ water. The reaction was carried out for two hours at room temperature (about 20° C. to about 22° C.). The excess unreacted compound was removed by dialyzing the samples overnight against 3×5 L 0.1 M sodium phosphate buffer, 0.15 M NaCl, pH 7.2 (phosphate buffered saline (PBS)). Three changes of PBS were used. Upon making a 1:100 dilution of the antibodies and performing an absorbance scan of the samples, a mole dye to mole protein ratio of about 5 was determined for both samples Ten mg goat anti-mouse IgG (H+L) (GAM) and 10 mg goat anti-rabbit IgG (H+L) (GAR) at 10 mg/ml were dialyzed overnight against 5 L 50 mM borate buffer, pH 8.4. The dialyzed antibodies were labeled with a 5 molar excess of the pure diastereomeric compound formula OB-5a with $X_1$=—NHS— that had been reconstituted in 0.1 ml MilliQ water. The reaction was carried out for two hours at room temperature. The excess unreacted compound was removed by dialyzing the samples overnight against 3×5 L of 0.1 M sodium phosphate buffer, 0.15 M NaCl, pH 7.2 (PBS). Three changes of PBS were used. Upon making a 1:100 dilution of the antibodies and performing an absorbance scan of the samples, a mole dye to mole protein ratio of about 2.5 was determined for both samples.

Ten mg streptavidin (SA) at 10 mg/ml was reconstituted in 50 mM borate buffer, pH 8.4. The streptavidin was labeled with a 5 molar excess of the diastereomeric compound formula OB-3a with $X_1$=—NHS— that had been reconstituted in 0.1 ml MilliQ water. The reaction was carried out for two hours at room temperature. The excess unreacted compound was removed by dialyzing the sample overnight against 3×5 L of 0.1 M sodium phosphate buffer, 0.15 M NaCl, pH 7.2 (PBS). Three changes of PBS were used. Upon making a 1:100 dilution of the antibody and performing an absorbance scan of the sample, a mole dye to mole protein ratio of about 4 was determined.

Ten mg streptavidin at 10 mg/ml was reconstituted in 50 mM borate buffer, pH 8.4. The streptavidin was labeled with a 4 molar excess of the pure diastereomeric compound formula OB-5a with $X_1$=—NHS— that had been reconstituted in 0.1 ml MilliQ water. The reaction was carried out for two hours at room temperature. The excess unreacted dye was removed by dialyzing the sample overnight against 3×5 L of 0.1 M sodium phosphate buffer, 0.15 M NaCl, pH 7.2 (PBS). Three changes of PBS were used. Upon making a 1:100 dilution of the antibody and performing an absorbance scan of the sample, a mole dye to mole protein ratio of about 2 was determined.

Ten mg NeutrAvidin® Biotin Binding Protein (NA) (Pierce Biotechnology, Inc.) at 10 mg/ml was reconstituted in 50 mM borate buffer, pH 8.4. The NeutrAvidin® Biotin Binding Protein was labeled with a 9 molar excess of the pure diastereomeric compound formula OB-3a with $X_1$=—NHS that had been reconstituted in 0.1 ml MilliQ water. The reaction was carried out for two hours at room temperature. The excess unreacted compound was removed by dialyzing the sample overnight against 3×5 L of 0.1 M sodium phosphate buffer, 0.15 M NaCl, pH 7.2 (PBS). Three changes of PBS were used. Upon making a 1:100 dilution of the antibody and performing an absorbance scan of the sample, a mole dye to mole protein ratio of about 3 was determined.

Ten mg NeutrAvidin® Biotin Binding Protein at 10 mg/ml was reconstituted in 50 mM borate buffer, pH 8.4. The NeutrAvidin® Biotin Binding Protein was labeled with a 4 molar excess of the pure diastereomeric compound formula OB-5a with $X_1$=—NHS, that had been reconstituted in 0.1 ml MilliQ water. The reaction was carried out for two hours at room temperature. The excess unreacted dye was removed by dialyzing the sample overnight against 3×5 L of 0.1 M sodium phosphate buffer, 0.15 M NaCl, pH 7.2 (PBS). Three changes of PBS were used. Upon making a 1:100 dilution of the antibody and performing an absorbance scan of the sample, a mole dye to mole protein ratio of about 2 was determined.

Example 7

Western Blots

Pure glutathione-S-transferase (GST) and lysates expressing GST were separated by electrophoresis on 4-20% Precise Protein gels. The proteins were transferred to an Immobilon-FL membrane (Millipore) and blocked overnight in 1×BSA/PBS-0.05% Tween.

Lanes 1 and 2 on each blot corresponded to yeast expressing GST (1:400 dilution) and Bir2 lysate expressing GST (1:400 dilution), respectively. Lanes 3 to 10 on each blot contained, respectively, 12.5 ng, 6.25 ng, 3.12 ng, 1.56 ng, 0.78 ng, 0.39 ng, 0.20 ng and 0.10 ng pure GST.

When using pure diasteromeric compound formula OB-3a, the blots were probed for one hour with rabbit-anti-GST primary antibody (0.2 µg/ml) or biotinylated anti-GST primary antibody (0.2 µg/ml) diluted in PBS-0.05% Tween-20. Following incubation, the blots were washed 3×10 min with PBS-0.05% Tween-20. Proteins were detected with goat-anti-rabbit (GAR) secondary antibody or streptavidin (SA) (0.04 µg/ml) or NeutrAvidine® (NA) (0.1 µg/ml) labeled with pure diasteromic compound formula OB-3a (0.04 µg/ml) diluted in PBS-0.05% Tween-20. After the incubation, all blots were washed 6×5 min with PBS-0.05% Tween-20. Images were captured on Typhoon 9410 Variable Mode Imager.

Results are shown in FIG. 1. FIG. 1 A was probed with rabbit anti-GST primary antibody (0.2 µg/ml) and detected with compound formula OB-3a labeled goat anti-rabbit (GAR) secondary antibody (0.04 µg/ml). FIGS. 1B and 1C were probed with biotinylated rabbit anti-GST primary antibody (0.2 µg/ml) and detected with compound formula OB-3a labeled SA (0.04 µg/ml) (FIG. 1B) or NA (0.1 µg/ml) (FIG. 1C). The data demonstrated that different secondary detection reagents labeled with compound formula OB-3a were able to detect antigens. The sensitivity of antigen detection was less than 1 ng.

When using pure diasteromeric compound formula OB-5a, the blots were probed with biotinylated anti-GST or rabbit anti-GST primary antibody (0.2 µg/ml). The blots were detected with fluorescently labeled goat anti-rabbit (GAR), SA, or NA (0.04 µg/ml).

Lanes 1 and 2 on each blot corresponded to Bir2 lysate expressing GST (1:400 dilution) and yeast expressing GST (1:400 dilution), respectively. Lanes 3 to 10 on each blot contained, respectively, 12.5 ng, 6.25 ng, 3.12 ng, 1.56 ng, 0.78 ng, 0.39 ng, 0.20 ng and 0.10 ng pure GST. Lane 11 contained a dual labeled molecular weight marker. Images were captured on the Typhoon 9410 Variable Mode Imager using the Cy5 setting.

Results for different secondary detection reagents labeled with compound formula OB-5a are shown in FIG. 2. FIGS. 2A and 2B were probed with biotinylated rabbit anti-BST primary antibody (0.2 µg/ml) and detected with compound formula OB-5a labeled SA (0.04 µg/ml) or NA (0.1 µg/ml). FIG. 2B was probed with rabbit anti-GST primary antibody (0.2 µg/ml) and detected with compound formula OB-5a labeled goat anti-rabbit antibody (0.04 µg/ml).

The data demonstrated that different secondary detection reagents labeled with compound formula OB-5a were able to detect antigens. The sensitivity of antigen detection was less than 1 ng.

Example 8

Fluorescence In-Situ Hybridization (FISH)

For cells with visible cytoplasm surrounding interphase and metaphase, slides are prepared by incubating the cells in 0.01 M HCl with 0.005% pepsin at 37° C. for ten minutes. The slides are then washed 2×1 minutes in PBS and incubated for ten minutes in 1% formaldehyde in PBS. The slides are incubated for 2×1 minute in PBS and then dehydrated in 70% ethanol for one minute, then at 95% ethanol for one minute, then at 100% ethanol for one minute, before air drying.

Ten µl of the compound formula OB-3a or the compound formula OB-5a labeled probe for each target is dispensed into a 0.5 ml microcentrifuge tube and then incubated at 96° C. for five minutes in a water bath. The tubes are briefly centrifuged, then 10 µl of the probe mix is applied to each target and covered with a coverslip. The slides and probes are denatured for two minutes at 80° C. on a temperature controlled hot plate and then incubated for 12-18 h in a humidified environment at 37° C.

The coverslip is removed by soaking in 2×SSC/0.1% Tween-20 at 37° C. The slide is then washed 4×5 min in 0.5×SSC/0.1% SDS at 60° C. to 65° C., and then briefly rinsed with distilled water and air dried out of direct light. DAPI anti-fade solution (20 µl) is applied to the target and covered with a coverslip (24 mm×50 mm) before viewing on a fluorescent microscope. Fluorescence will be detected with hydridization occurs.

Example 9

Microarrays

Microarray analysis of Interleukin (IL)-2, IL-8, IL-12p70, and tumor necrosis factor (TNF)α was performed using human Inflammation I Array (Pierce Biotechnology, Inc.) with standards supplied. Rabbit antibodies for IL-2 and IL-8, and biotinylated mouse antibodies for IL-12p70 and TNFα were diluted to 1 µg/ml in 1% BSA/dPBS and then used as detection antibodies. Compound formula OB-3a and compound formula OB-5a conjugates of goat anti-rabbit (GAR), streptavidin (SA), and NeutrAvidin® (NA) were diluted to 0.1 µg/ml and then used for fluorescent detection of the probes.

Glass slides containing a microarray of human inflammatory proteins were equilibrated to room temperature in a desiccator. The slides were blocked for fifteen min using 1% bovine serum albumin (BSA)/5% sucrose/Dulbecco's phosphate buffered saline (DPBS) in screw cap slide holders and then dried in a slide centrifuge for thirty sec. Slide overlays were placed on the blocked slides and rinsed once with PBS containing 0.05% Tween-20 (PBST).

The antigen set was applied for two hours at 50 µl of a 1000 pg/ml stock solution per subarray. The slides were rinsed three times with PBST. Rabbit antibodies for IL-2 and IL-8, and biotinylated mouse antibodies for IL-12p70 and TNFalpha were applied for one hour at 50 µl of a 1 µg/ml stock solution. The slide was rinsed three times with PBST. The pure diasteromeric compound formula OB-3a and compound formula OB-5a conjugates of goat anti-rabbit, SA, and NA were applied for one hour at 50 µl of a 0.1 µg/ml stock solution. The slides were washed five times with PBST, removed from the frame, and dipped in 0.25×PBS for 5 sec. and then dried by centrifugation for about 30 sec.

Results were visualized using the Alpha Innotech AlphaScan™ Imager (Alpha Inotech Corp.), and are shown for compound formula OB-3a conjugates in FIG. 3, and for compound formula OB-5a conjugates in FIG. 4.

Figure 3B:
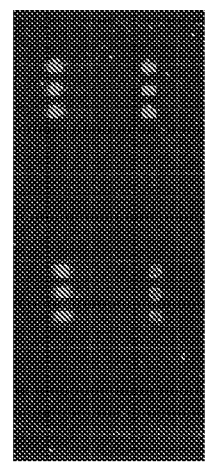
Figure 3C:
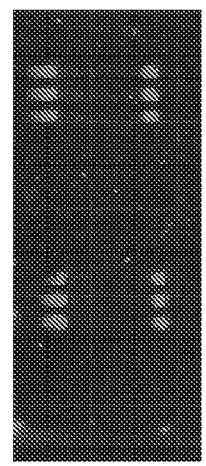

FIG. 3A shows detection of IL-2 and IL-8 on microarrays probed with a 1:10,000 dilution of compound formula OB-3a-GAR. FIGS. 3B and 3C show detection of IL-12p70 and TNFα on microarrays probed with 1:10,000 dilutions of compound formula OB-3a-SA (FIG. 3B) and compound formula OB-3a-NA (FIG. 3C). The data demonstrated use of compound formula OB-3a conjugates to detect human inflammatory proteins such as IL-2, IL-8, IL-12p70, and TNFα in samples on microarrays.

FIG. 4A shows a human inflammation I array probed for IL-2, IL-8, IL-12p70, and TNFα with primary antibodies, or biotinylated primary antibodies for detection with biotin-binding proteins, corresponding to these antigens at 1 µg/ml, followed by a 1:10,000 dilution of compound formula OB-5a-GAR. FIGS. 4B and 4C show human inflammation I arrays probed with 1:10,000 dilutions of compound formula OB-5a-SA (FIG. 4B) and compound formula OB-5a-NA (FIG. 4C). The data demonstrated that antibodies and biotin-binding protein secondary detection reagents labeled with compound formula OB-5a, when used together with primary antibodies, detected specific antigens in samples on microarrays.

Example 10

Immunofluorescence

Histological slides of Ki-67 and S100 human colon adenocarcinoma tissue were prepared according to the manufacturer's instructions (Dako, Glostrup Denmark). Slides were blocked with 3% goat serum in PBST overnight. A mouse antibody raised against human Ki-67 and a rabbit antibody raised against S100 were diluted 1:75 and 1:400, respectively, from the original concentrations. Detection was carried out with a goat anti-mouse conjugate of compound formula OB-5a (red) and a goat anti-rabbit conjugate of compound formula OB-3a (green). Slides were deparraffinized by heating at 45° C. for 50 min in an incubator. The tissue was rehydrated with two, five minute incubations in EZ-dewax solution (Dako) and then washed once with ultrapure water and once with phosphate buffered saline-Tween (PBST).

The targets were retrieved by incubating the slide in Target Retrieval Solution (Dako) at 95-99° C. for 40 min, followed by cooling to room temperature for 20 minutes and rinsing once with PBST. The tissue was washed two times for three minutes each with PBST. The slide containing the tissue was returned to the original boxes and 15 mL of 3% normal goat serum in PBST was added. The slide incubated at 4° C. overnight, then was dried by centrifugation.

Mouse anti-human Ki-67 and rabbit anti-S100 primary antibodies were diluted 1:75 and 1:400 (from the original concentrations); 200 µl was applied to the slide containing the tissue. The tissue was covered with an incubation chamber to prevent evaporation of the antibody solution, and incubated for one hour with the primary antibodies. The slide containing the tissue was passively washed three times with PBST.

Compound formula OB-5a labeled conjugate of goat anti-mouse and compound formula OB-3a labeled conjugate of goat anti-rabbit were diluted to 0.01 µg/ml and 200 µl was applied to the slide. The tissue was covered within an incubation chamber to prevent evaporation of antibody solution. The slide was incubated for one hour with the secondary antibodies, then was passively washed three times with PBST. The slide was dipped in PBS and then dried by centrifugation. One drop of fluorescence mounting medium was added to the slide, and a coverslip was applied. The slide was stored at 4° C. until visualization on a Zeiss confocal microscope.

Figure 5:
FIG. 5 shows multiplexing immunofluorescence of tissue using two different primary antibodies with corresponding secondary antibodies conjugated to different compounds (formula OB-3a and formula OB-5a).

FIG. 5 shows immunofluorescence multiplexing of tissue, using two different primary antibodies made in different species, followed by corresponding secondary antibodies conjugated to different compounds (formula OB-3a and formula OB-5a). The data demonstrated specific detection of Ki-67 with compound formula OB-3a labeled antibody, and specific detection of S100 with compound formula OB-5a labeled antibody.

Example 11

Microwell Plate Based Assays

Streptavidin and NeutrAvidin® Conjugates.

Plate based assays were performed on serially diluted 96-well white opaque biotinylated-BSA coated plates (2 µg/ml to 0 µg/ml). Plates were washed three times with 200 µl PBS containing 0.05% Tween and one time with 200 µl with PBS. Compound formula OB-3 and compound formula OB-5a-labeled streptavidin (SA) and NeutrAvidine® (NA) conjugates were diluted 0.004 mg/ml in PBS and applied to the wells of the plates (100 µl/well). Plates, covered and protected from light, were incubated for one hour and then washed as in Example 10. PBS was added to the plates (100 µl/well) and the fluorescent intensity was captured using the Tecan Safire at Cy3 and Cy5 settings.

Figure 6B:
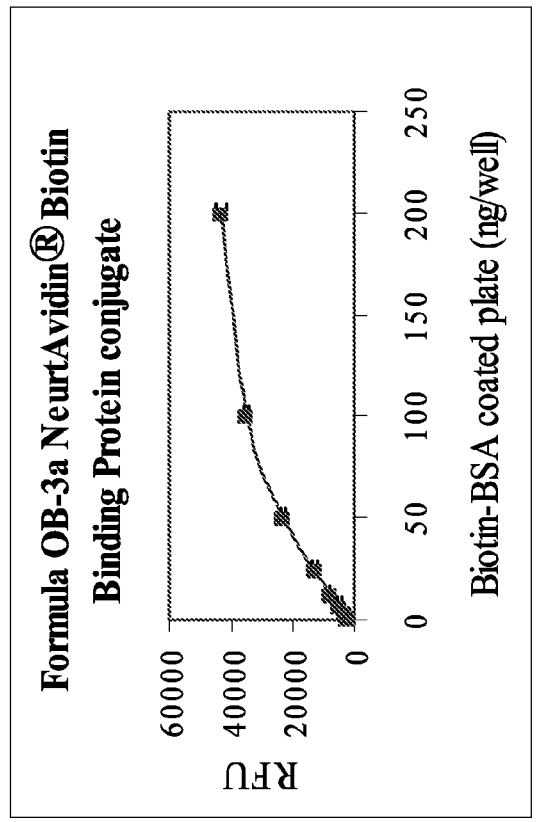
FIGS. 6A, 6B show biotinylated protein coated microwell plates detected with biotin-binding protein conjugates of one compound (formula OB-3a).
Figure 6A:
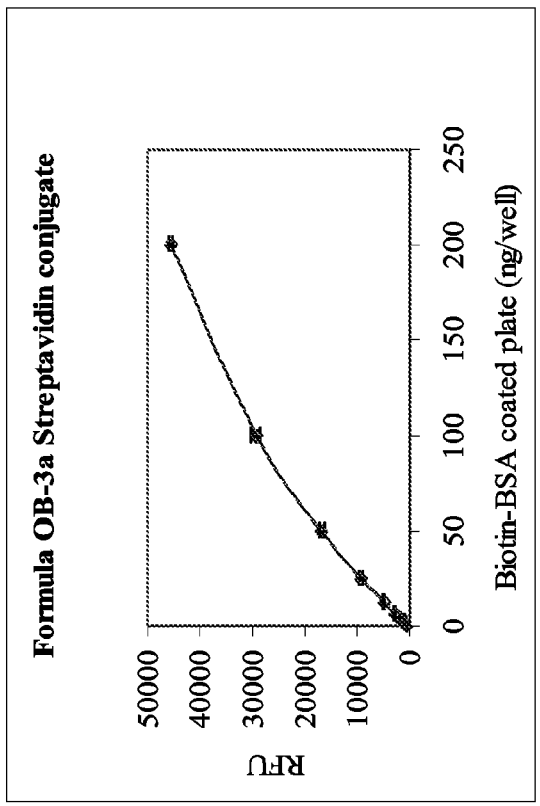

Results for biotinylated bovine serum albumin (BSA)-coated microwell plates detected with biotin-binding protein conjugates of compound formula OB-3a and compound formula OB-5a are shown in FIG. 6. FIG. 6A shows compound formula OB-3 conjugated to SA. With this conjugate, detection sensitivity to 3 ng biotinylated BSA was achieved. FIG. 6B shows compound formula OB-3a conjugated to NA. With this conjugate, detection sensitivity to 3 ng biotinylated BSA was achieved. These data demonstrated that biotin-binding proteins conjugated to compound formula OB-3a detected biotinylated proteins in plate based assays.

Figure 7:
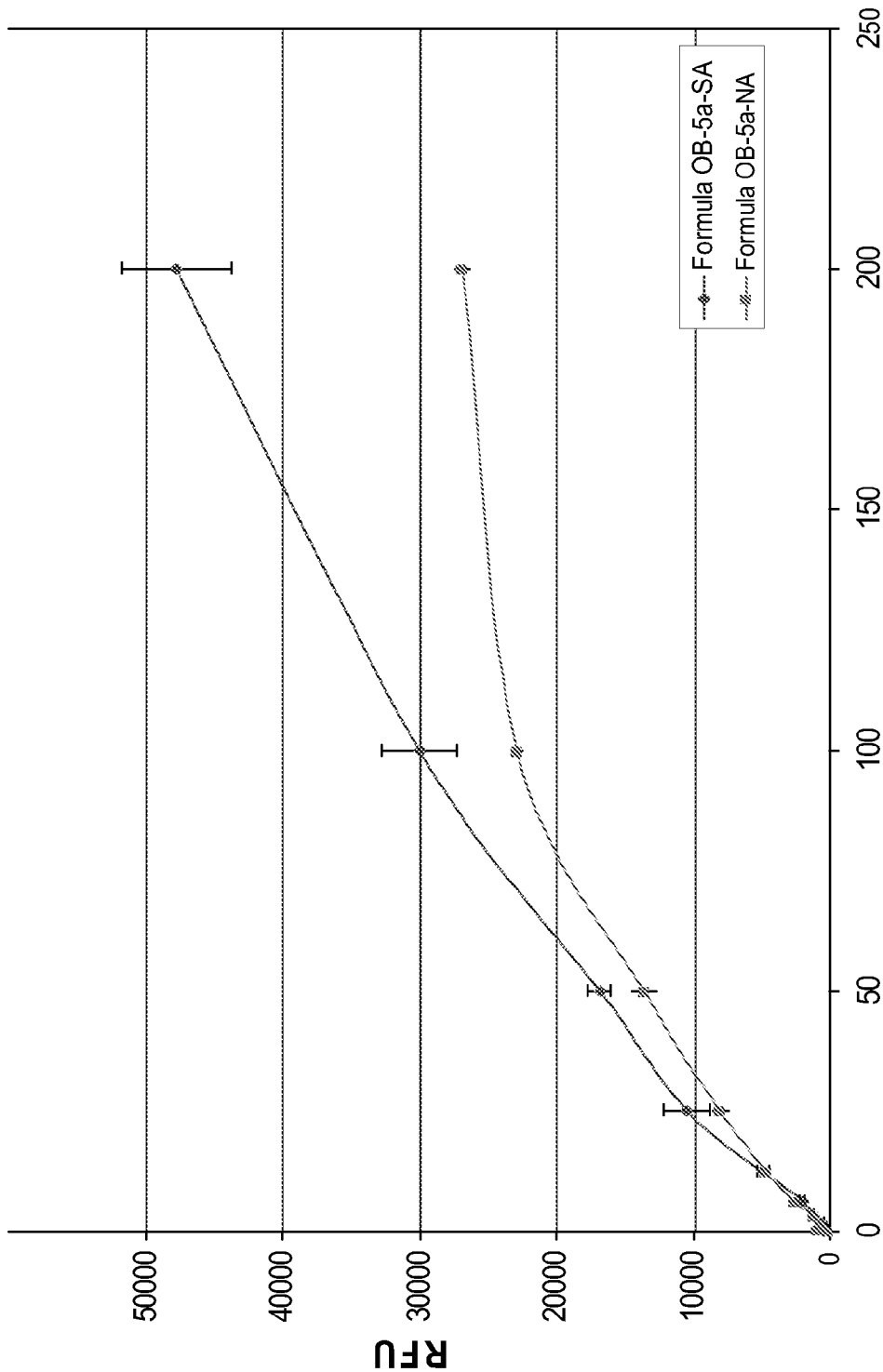
FIG. 7 shows biotinylated protein coated microwell plates detected with biotin-binding protein conjugates of another compound (formula OB-5a).

Microplates were coated with biotinylated (BSA) (BBSA) at concentrations shown in FIG. 7. Compound formula OB-5a conjugates of SA and NA were diluted 1:250 from 1 mg/ml stock solutions in PBS, and 100 µl was applied to each plate. Fluorescent intensity was measured with a Tecan Safire Microplate Reader using the Cy5 Dye setting.

Results for biotinylated BSA-coated microwell plates detected with biotin-binding protein conjugates of compound formula OB-5a are shown in FIG. 7. The data demonstrated that compound formula OB-5a conjugated to SA detected less than 1 ng biotinylated BSA in a plate based, and that compound formula OB-5a conjugated to NA detected about 3 ng biotinylated BSA in a plate based assay.

Goat Anti-Mouse and Goat Anti-Rabbit Conjugates.

Functional assays were performed on serially diluted 96-well white opaque mouse IgG or rabbit IgG coated plates (10 µg/ml to 0 µg/ml). Plates were washed three times with 200 µl PBS containing 0.05% Tween and one time with 200 µl PBS. Compound formula OB-3a and compound formula OB-5a-goat anti-mouse (GAM) and goat anti-rabbit (GAR) conjugates were diluted 0.004 mg/ml in PBS. Diluted conjugates were applied to the wells of the plates (100 µl/well). Plates, covered and protected from light, were incubated for one hour and then washed as in Example 10. PBS was added to the plates (100 µl/well) and the fluorescent intensity was captured using the Tecan Safire at green laser setting.

Figure 8B:
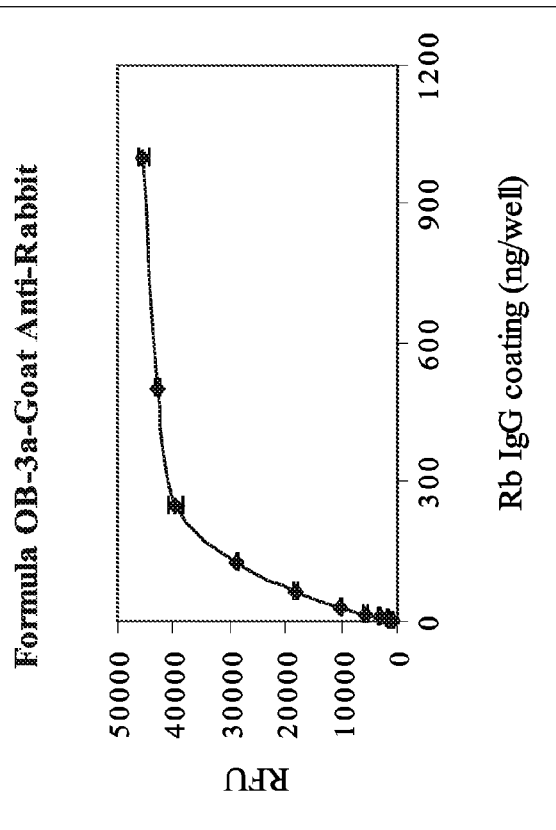
FIG. 8 shows mouse immunoglobulin (FIG. 8A) and rabbit immunoglobulin (FIG. 8B) coated microwell plates detected with conjugates of one compound (formula OB-3a).
Figure 8A:
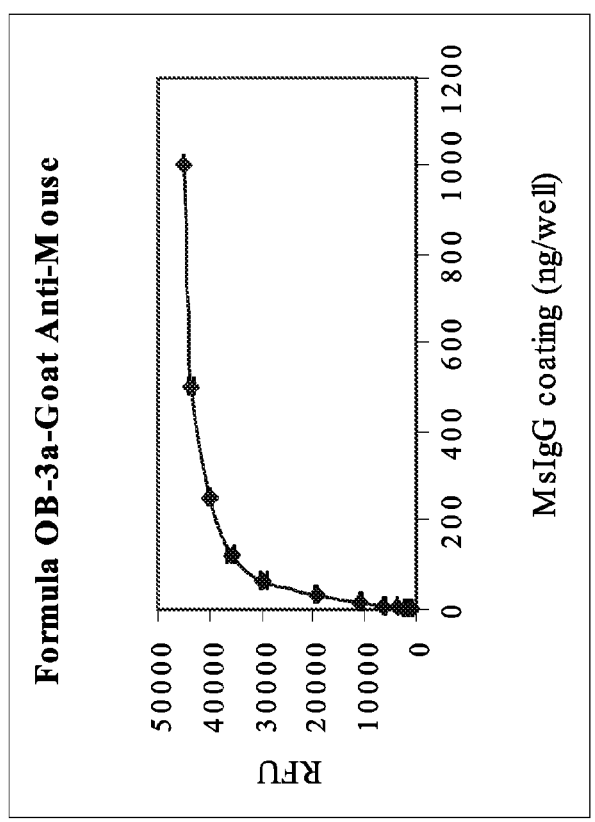

Results for compound OB-3a conjugated GAM and GAR are shown in FIG. 8. FIG. 8A shows compound formula OB-3a conjugated to goat anti-mouse antibodies. The data demonstrated detection sensitivity in the low nanogram range for mouse IgG with compound formula OB-3a conjugated GAM. FIG. 8B shows compound formula OB-5a conjugated to goat anti-rabbit. The data demonstrated detection sensitivity in the low nanogram range for rabbit IgG with compound formula OB-3a conjugated GAR.

Figure 9:
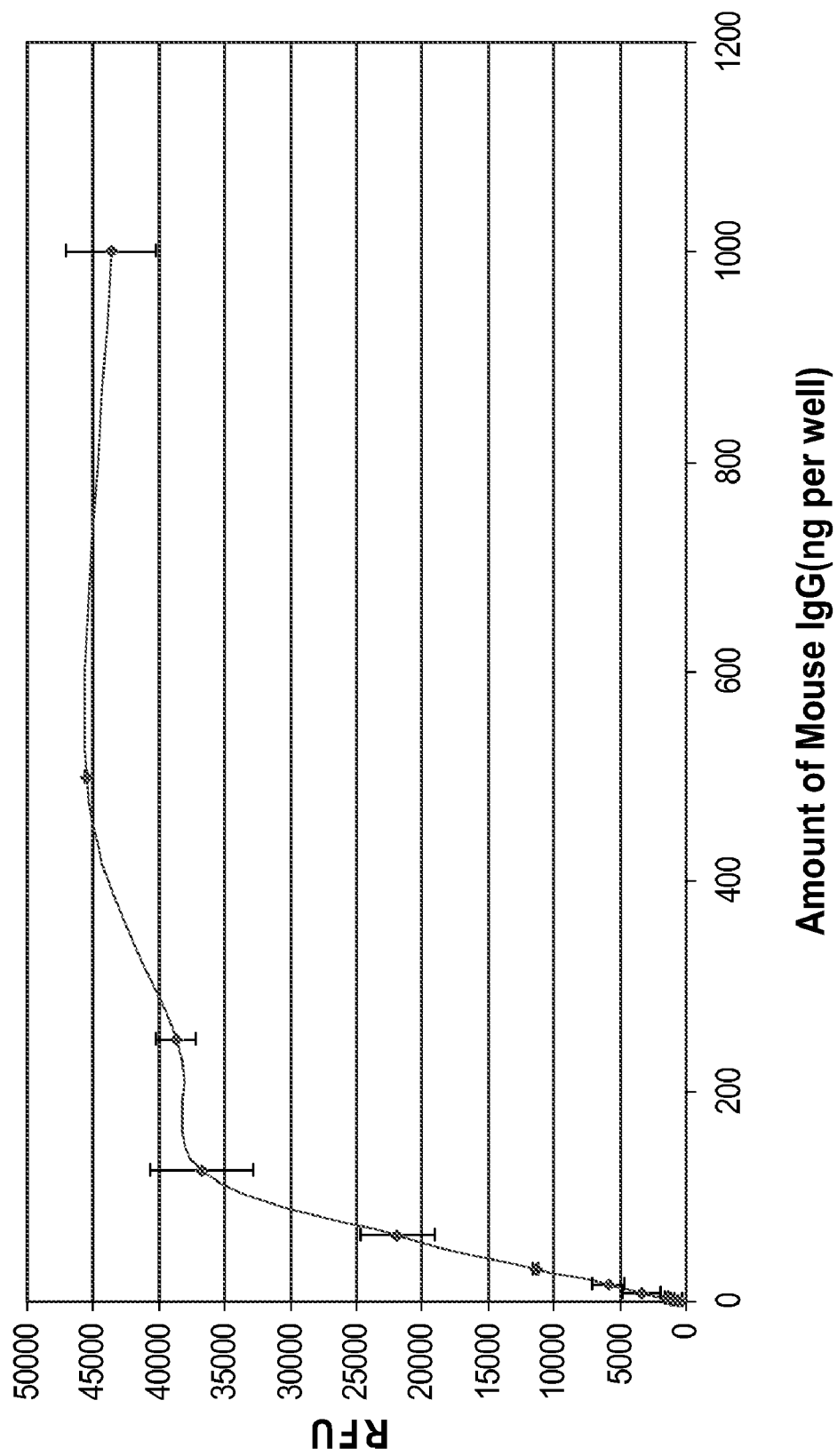
FIG. 9 shows mouse immunoglobulin coated microwell plates detected with conjugates of another compound (formula OB-5a).

Microplates were coated with mouse IgG at the concentration indicated at FIG. 9. A compound formula OB-5a conjugate of GAM was diluted 1:250 from 1 mg/ml stock solution in PBS, and 100 µl was applied to each plate. Fluorescent intensity was measured with a Tecan Safire Microplate Reader using the Cy5 Dye setting.

Results for compound formula OB-5a conjugated to GAM are shown in FIG. 9. The data demonstrated detection sensitivity in the low nanogram range of mouse IgG with compound formula OB-5a conjugated to GAM.

Figure 10:
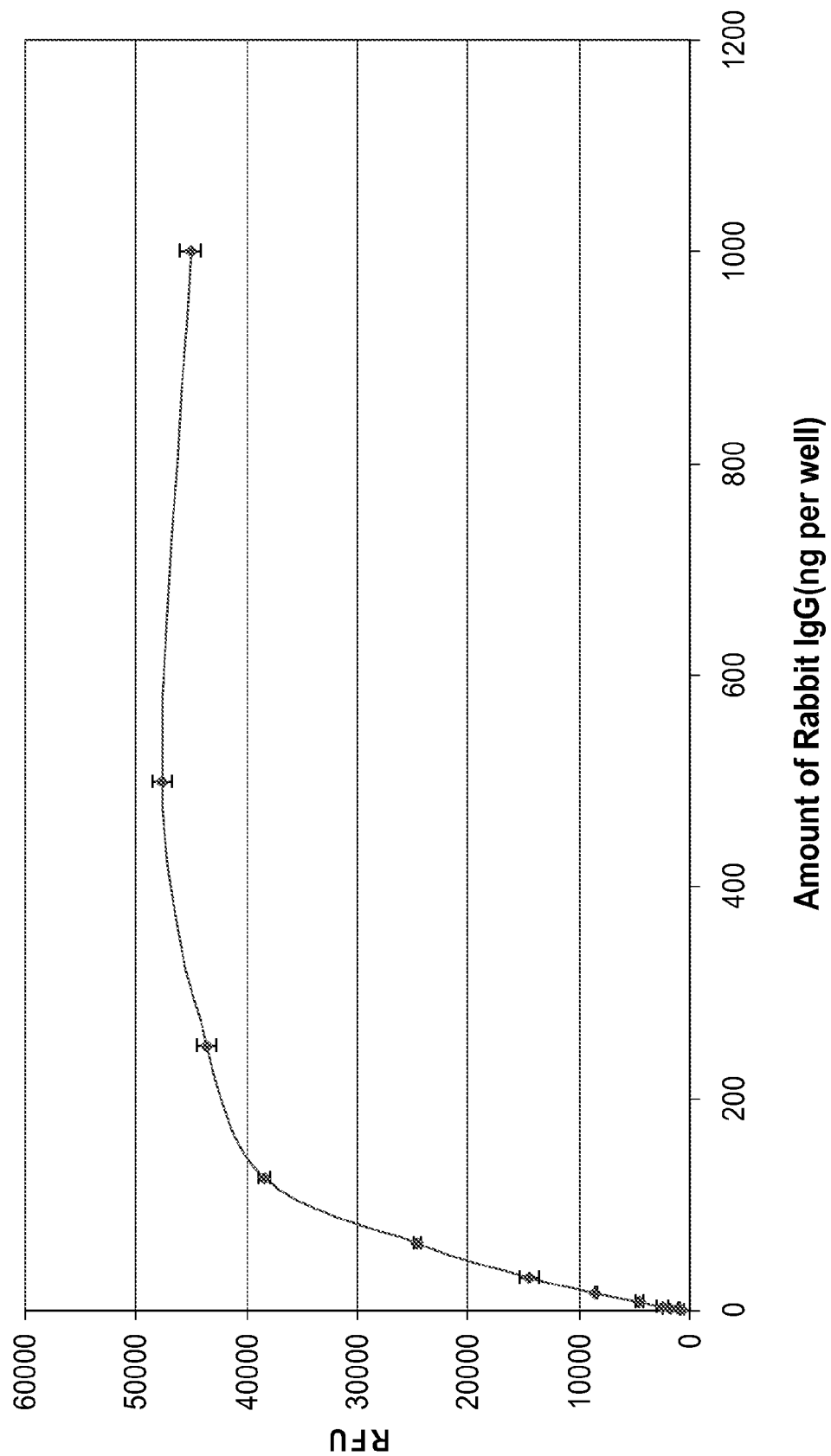

Microplates were coated with rabbit IgG at the concentration indicated at FIG. 10. A compound formula OB-5a conjugate of GAR was diluted 1:250 from 1 mg/ml stock solution in PBS, and 100 µl was applied to each plate. Fluorescent intensity was measured with a Tecan Safire Microplate Reader using the Cy5 Dye setting.

Results for compound formula OB-5a conjugated to GAR are shown in FIG. 10. The data demonstrated detection sensitivity in the low nanogram range of rabbit IgG with compound formula OB-5a conjugated to GAR.

Example 13

Flow Cytometry

Flow cytometry was used to evaluate CD3 receptor on Jurkat cells with a compound formula OB-5a labeled goat anti-mouse secondary antibody.

Jurkat cells were centrifuged for five minutes at 4000 rpm, washed with 1×3 ml dPBS, and resuspended in 5 ml dPBS. Cell concentration was adjusted to $28 \times 10^6$ cells/ml. Cells were incubated for 45 min in mouse anti-CD3 antibody (0.625 µg/ml), centrifuged for five min and washed with 2×1 ml PBS. Cells were incubated for 45 min in compound formula OB-5a labeled goat anti-mouse diluted in dPBS (2.7 µg/ml).

Cells were then centrifuged as previously described, washed 2×1 ml in dPBS, and resuspended in 300 µl dPBS. Data were collected on a Becton Dickinson FACSCalibur® flow cytometer with four color fluorescence capability.

Figure 11:
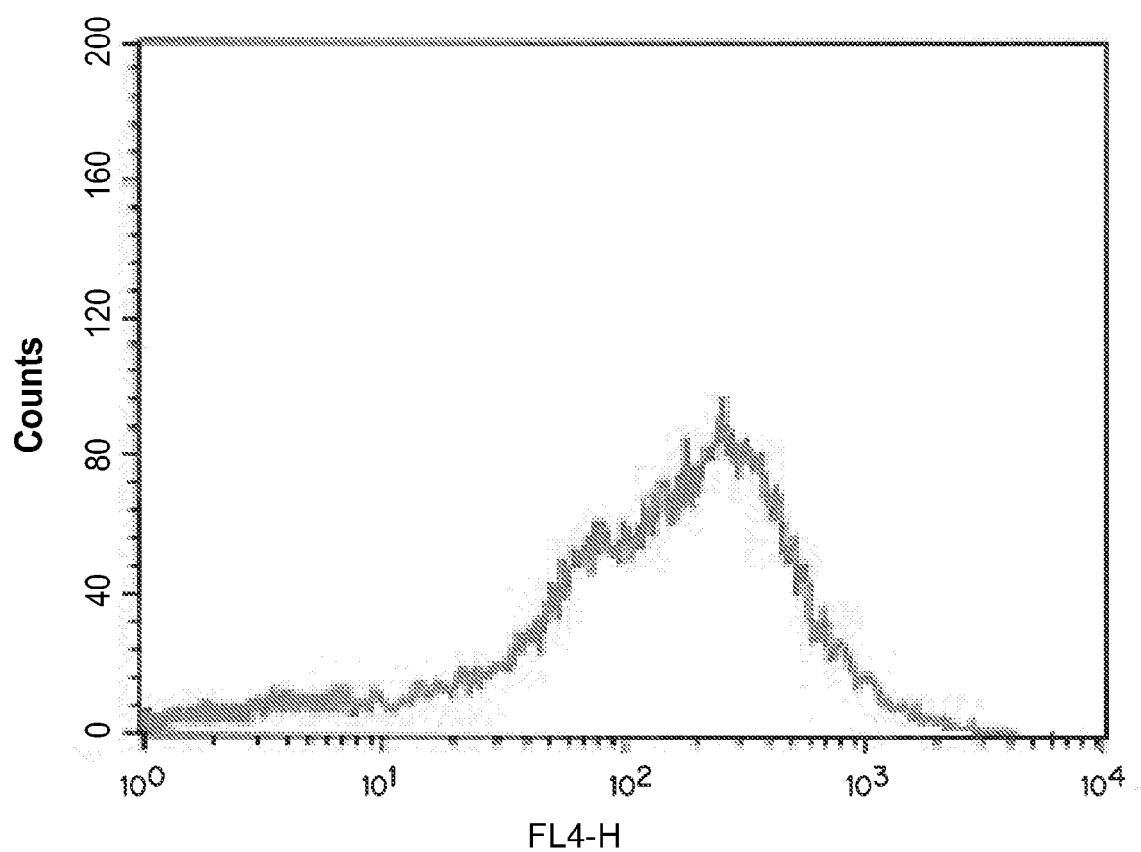
FIG. 11 shows flow cytometry data for one cell type using a conjugate of one compound (formula OB-5a).

Results are shown in FIG. 11. The data demonstrated utility of compound formula OB-5a conjugated secondary detection reagent in flow cytometry applications.

Example 12

High Throughput Screening

Functional assays were performed on serially diluted 96-well white opaque biotinylated-BSA coated plates (2 µg/ml to 0 µg/ml). Plates were washed three times with 200 µl PBS containing 0.05% Tween and one time with 200 µl PBS. Formula OB-5a streptavidin (SA) and Alexa® 647 (Invitrogen, Carlsbad Calif.)—SA conjugates were diluted 0.004 mg/ml in PBS. Diluted conjugates were applied to the wells of the plates (100 μl/well). Plates, covered and protected from light, were incubated for one hour and then washed as in Example 10. PBS was added to the plates (100 μl/well) and the fluorescent intensity was captured using the Tecan Safire at Cy5 setting.

Figure 12:
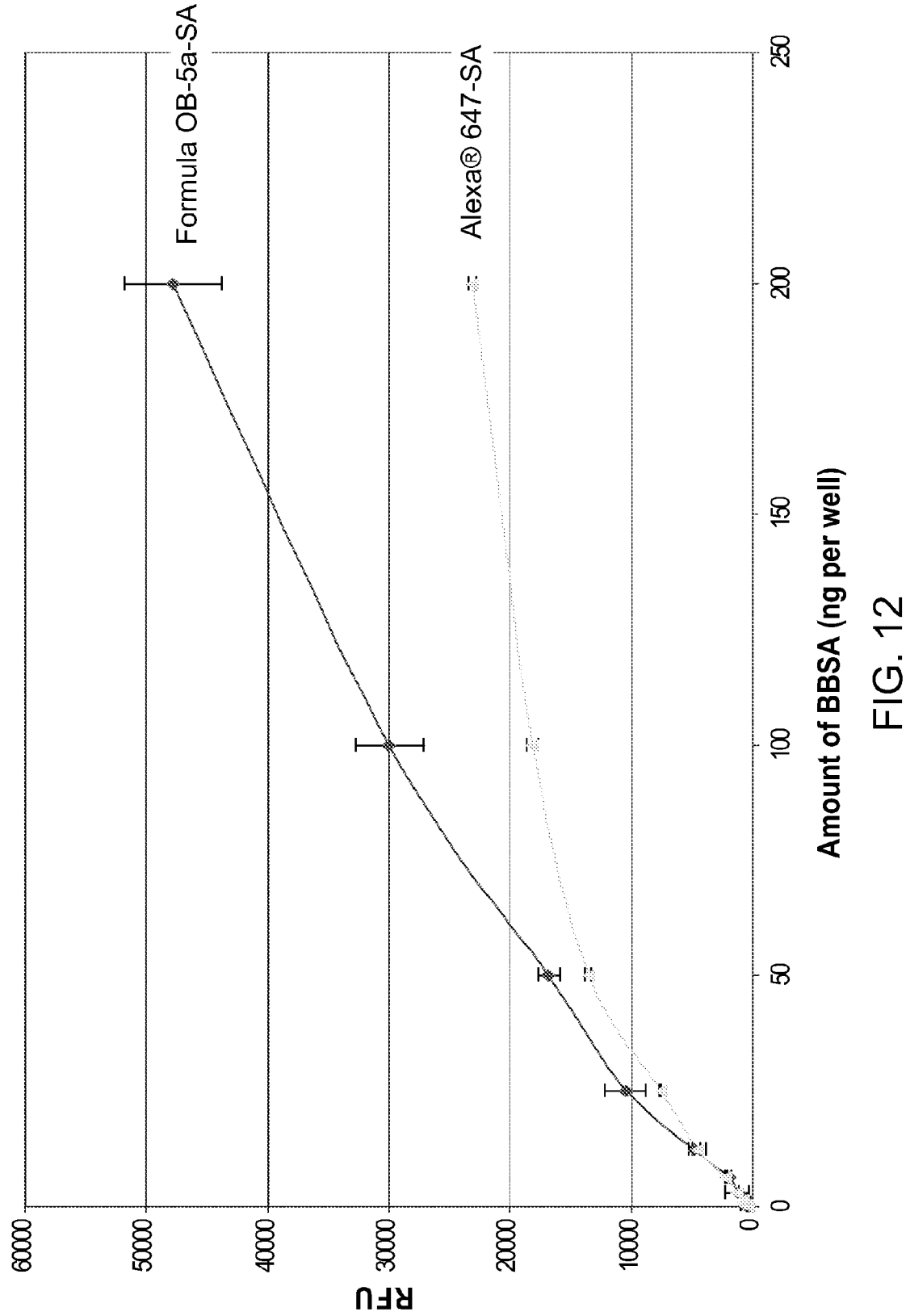
FIG. 12 shows comparison of streptavidin conjugated to a commercially available dye and one compound (formula OB-5a) binding to a biotinylated protein coated microwell plate.

Results are shown in FIG. 12. The data demonstrated that a significantly higher signal to noise ratio was obtained with compound formula OB-5a conjugated SA compared to Alexa® 647 conjugated SA.

Example 13

Use Of Diastereomers As Labels

Ten mg streptavidin (SA) at 10 mg/ml is reconstituted in 50 mM borate buffer, pH 8.4. SA is labeled with a 5 molar excess of the pure diastereomeric compound formula OB-3a with $X_1$=—NHS that is reconstituted in 0.1 ml MilliQ water. The reaction is carried out for two hours at room temperature. The excess unreacted compound is removed by dialyzing the sample overnight against 3×5 L of 0.1 M sodium phosphate buffer, 0.15 M NaCl, pH 7.2 (PBS). Three changes of PBS are used.

Ten mg streptavidin at 10 mg/ml is reconstituted in 50 mM borate buffer, pH 8.4. SA is labeled with a 4 molar excess of the pure diastereomeric compound formula OB-5a with $X_1$=—NHS that is reconstituted in 0.1 ml MilliQ water. The reaction is carried out for two hours at room temperature. The excess unreacted dye is removed by dialyzing the sample overnight against 3×5 L of 0.1 M sodium phosphate buffer, 0.15 M NaCl, pH 7.2 (PBS). Three changes of PBS are used.

It should be understood that the embodiments and examples described are only illustrative and are not limiting in any way. For example, any of OB-3a, OB-3b, OB-5a, and/or OB-5b may be used in the above examples. Therefore, various changes, modifications or alterations to these embodiments may be made or resorted to without departing from the spirit of the invention and the scope of the following claims.

What is claimed is:
1. An isolated enantiomeric mixture selected from diastereomer Ia,

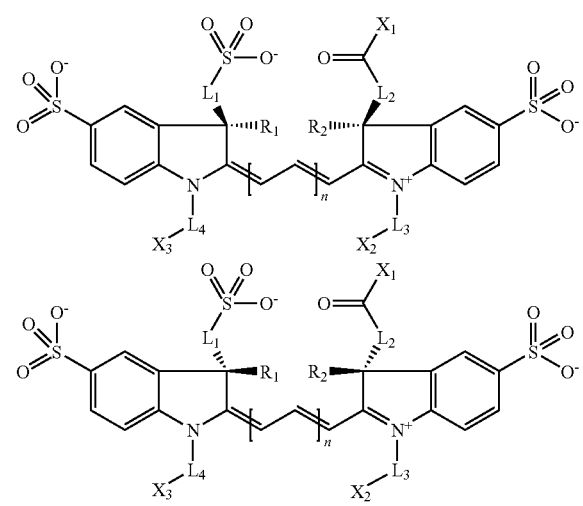

diastereomer Ib,

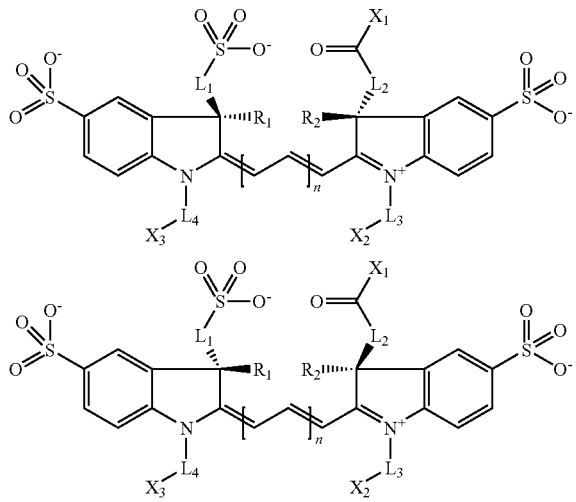

diastereomer IIa,

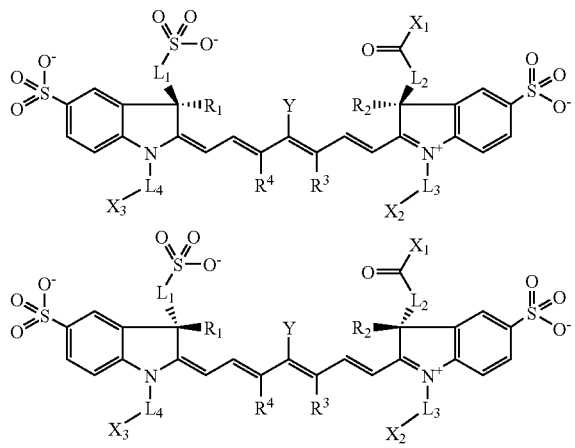

or, diastereomer IIb,

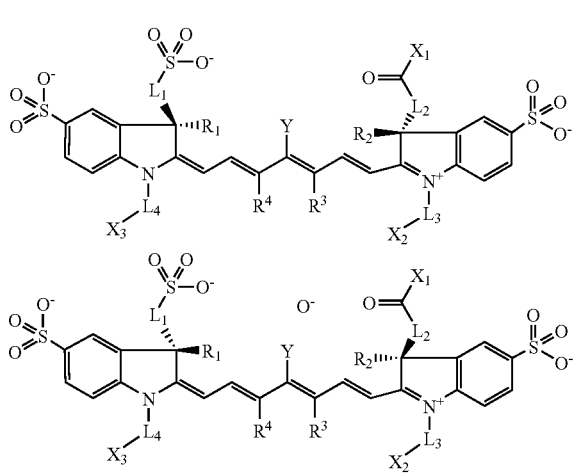

whereby diastereomers Ia and Ib are derived from general formula I

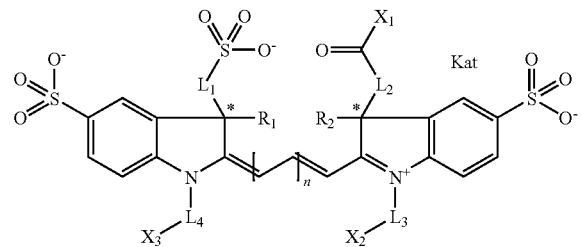

and diastereomers IIa and IIb are derived from general formula II,

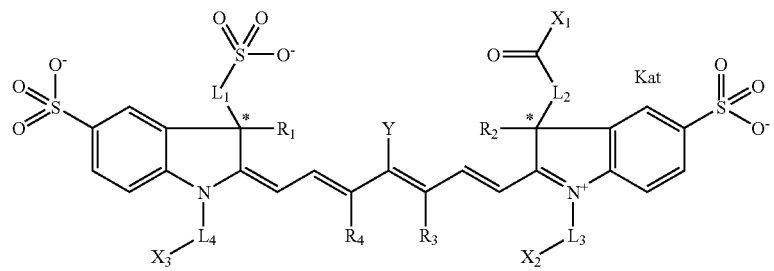

and whereby each of $R^1$ and $R^2$ is the same or different and is independently selected from the group consisting of an aliphatic and heteroaliphatic group;

each of $L_1$ to $L_4$ is the same or different and is independently selected from the group consisting of a divalent linear (—(—$CH_2$)$_o$—, o=1 to 15), crossed, or cyclic alkylene group which can be substituted by at least one atom selected from the group consisting of oxygen, substituted nitrogen, and sulfur;

$X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-$CO_2$—NHS, —NR-L-$CO_2$-STP, —NR-L-$CO_2$-TFP, —NR-L-CO-benzotriazole, —NR-L-CHO, —NR-L-maleimid, and —NR-L-NH—CO—$CH_2$—I, R is —H or is equal to $R^1$ or $R^2$, and L is equal to $L_1$ to $L_4$;

each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto-, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof;

Kat is a number of $Na^+$, $K^+$, $Ca^{2+}$, ammonia, or other cation(s) needed to compensate the negative charge brought by the cyanine;

n in formula I is a integer from 0 to 3;

Y in formula II is selected from the group consisting of fluorine, chlorine, bromine, a substituted phenoxy-, and a substituted arylmercapto-(phenyl sulfanyl-) function; and each of $R^3$ and $R^4$ in formula II is the same or different and is independently an aliphatic or heteroaliphatic group respectively, or forms together the divalent structural element selected from the group consisting of —$(CH_2)_m$—, —$(CH_2)_mO(CH_2)_{m'}$—, —$(CH_2)_mS(CH_2)_{m'}$—, —$(CH_2)_m$CH=CH—, and —OCH=CH— where each of m and m' is the same or different and is a integer from 2 to 6.

2. The diastereomer of claim 1 conjugated to a biomolecule selected from at least one of a protein, antibody, enzyme, nucleoside triphosphate (NTP), oligonucleotide, biotin, hapten, cofactor, lectin, antibody binding protein, carotenoid, hormone, neurotransmitter, growth factors, toxin, biological cell, lipid, receptor binding drug, organic polymer carrier material, or inorganic polymeric carrier material.

3. A biocompatible dye composition comprising at least one excipient and an isolated enantiomeric mixture selected from diastereomer Ia,

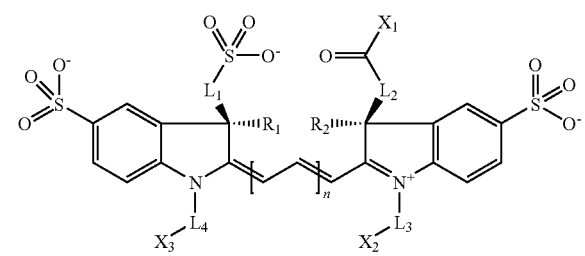

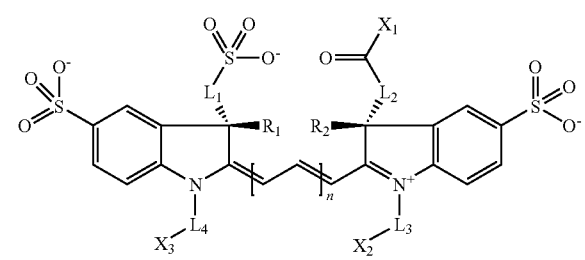

diastereomer Ib,
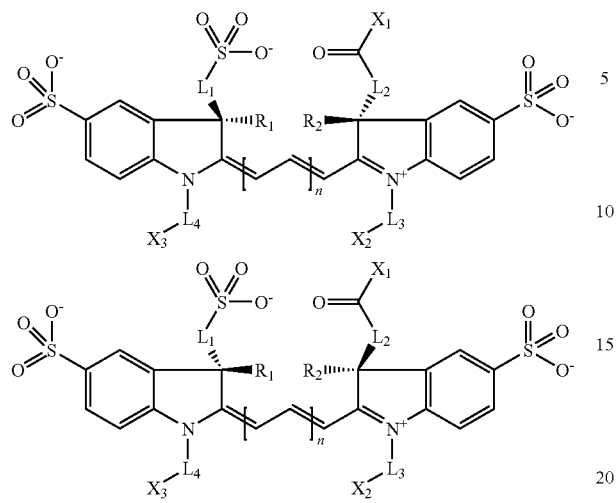
diastereomer IIa,
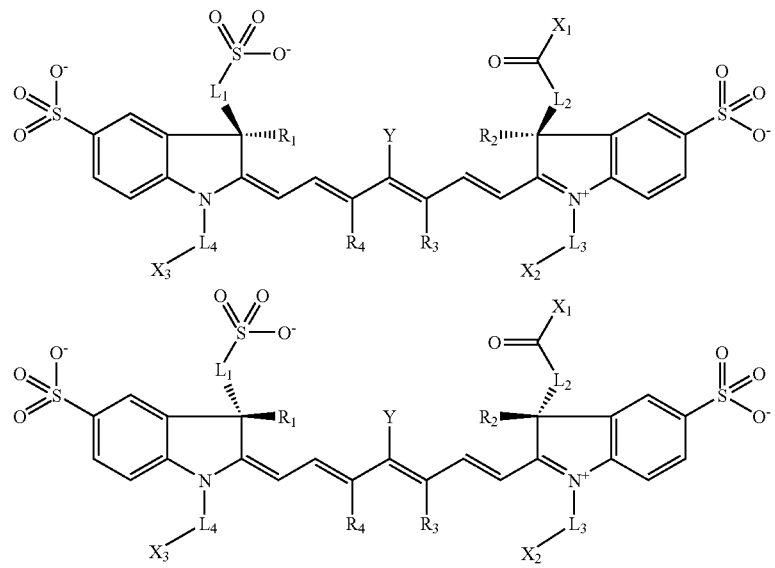
or, diastereomer IIb,
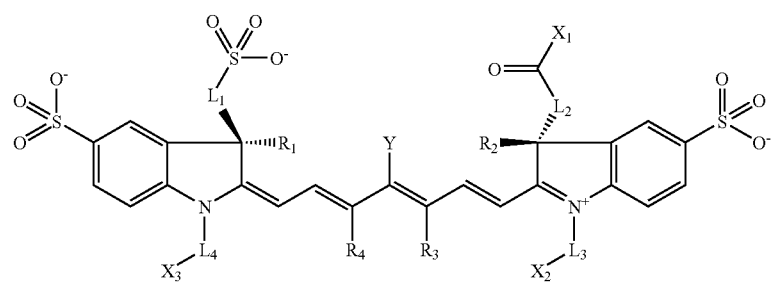

-continued

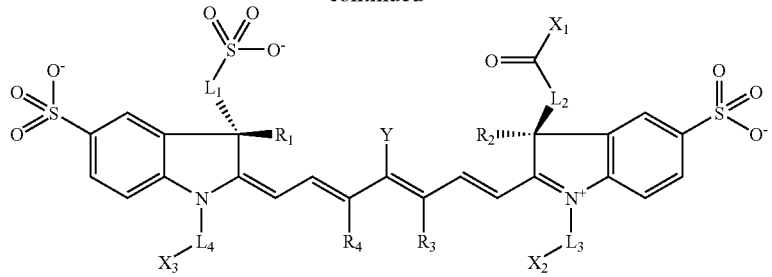

whereby diastereomers Ia and Ib are derived from general formula I

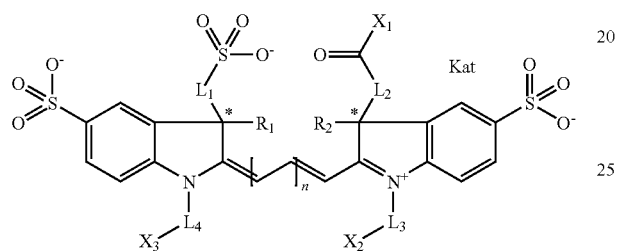

and diastereomers IIa and IIb are derived from general formula II,

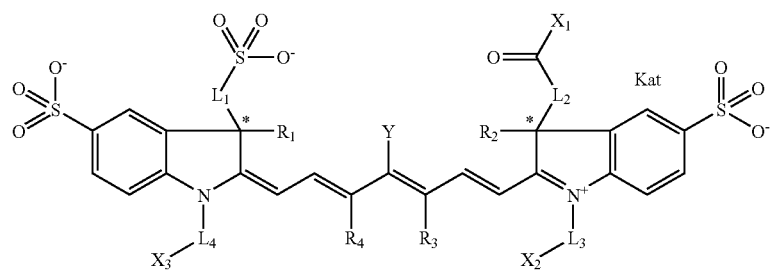

and whereby each of $R^1$ and $R^2$ is the same or different and is independently selected from the group consisting of an aliphatic and heteroaliphatic group;

each of $L_1$ to $L_4$ is the same or different and is independently selected from the group consisting of a divalent linear (—$(CH_2)_o$—, o=1 to 15), crossed, or cyclic alkylene group which can be substituted by at least one atom selected from the group consisting of oxygen, substituted nitrogen, and sulfur;

$X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-$CO_2$—NHS, —NR-L-$CO_2$—STP, —NR-L-$CO_2$-TFP, —NR-L-CO-benzotriazole, —NR-L-CHO, —NR-L-maleimid, and —NR-L-NH—CO—$CH_2$—I, R is —H or is equal to $R^1$ or $R^{2'}$ and L is equal to $L_1$ to $L_4$;

each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof;

Kat is a number of $Na^+$, $K^+$, $Ca^{2+}$, ammonia, or other cation(s) needed to compensate the negative charge brought by the cyanine;

n in formula I is a integer from 0 to 3;

Y in formula II is selected from the group consisting of fluorine, chlorine, bromine, a substituted phenoxy-, and a substituted arylmercapto-(phenyl sulfanyl-) function; and each of $R^3$ and $R^4$ in formula II is the same or different and is independently an aliphatic or heteroaliphatic group respectively, or forms together the divalent structural element selected from the group consisting of —$(CH_2)_m$—, —$(CH_2)_mO(CH_2)_{m'}$—, —$(CH_2)_mS(CH_2)_{m'}$—, —$(CH_2)_mCH=CH$—, and —OCH=CH— where each of m and m' is the same or different and is a integer from 2 to 6.

4. The composition of claim 3 wherein the diastereomer is conjugated to a biomolecule selected from at least one of a protein, antibody, enzyme, nucleoside triphosphate (NTP), oligonucleotide, biotin, hapten, cofactor, lectin, antibody binding protein, carotenoid, hormone, neurotransmitter, growth factors, toxin, biological cell, lipid, receptor binding drug, organic polymeric carrier material, or inorganic polymeric carrier material.

5. A method of labeling at least one biomolecule, the method comprising provided a composition comprising at least one excipient and one isolated enantiomeric mixture in an effective concentration to at least one biomolecule under conditions sufficient for binding the enantiomeric mixture to the biomolecule, and detecting the biomolecule-bound enantiomeric mixture, where the one isolated enantiomeric mixture is diastereomer Ia

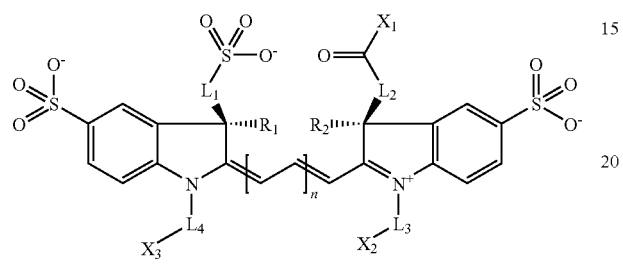

diastereomer Ib

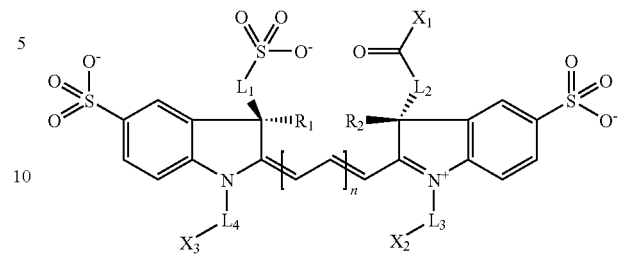

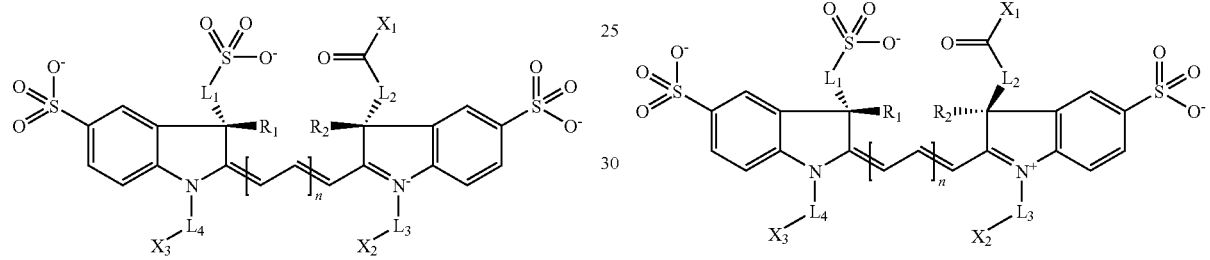

diastereomer IIa,

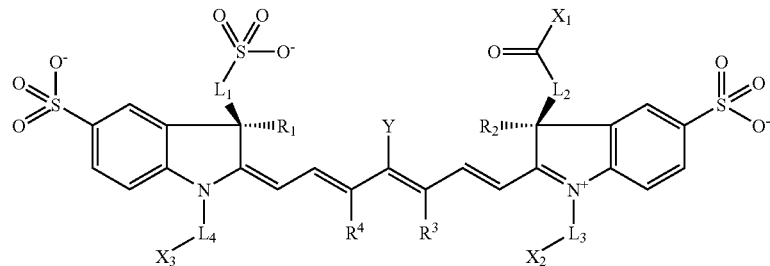

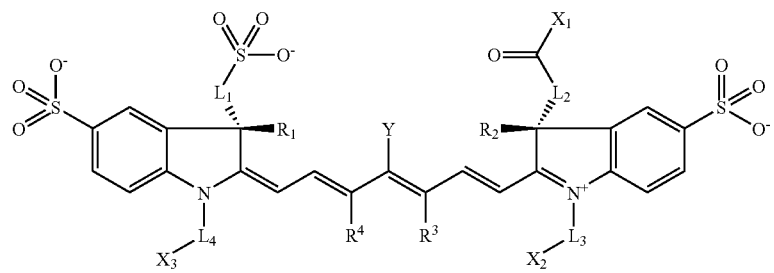

or, diastereomer IIb,

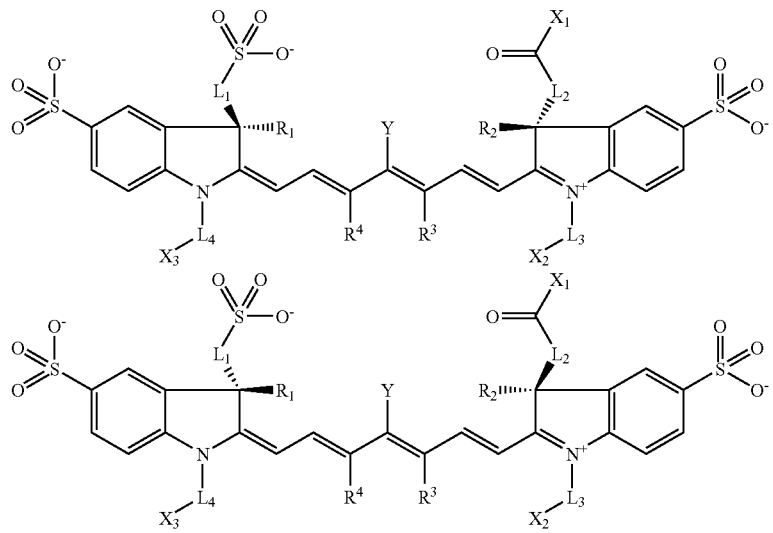

whereby diastereomers Ia and Ib are derived from general formula I

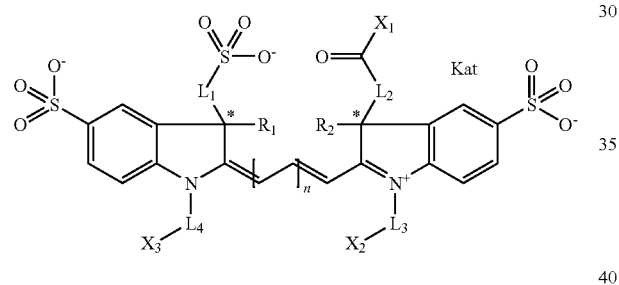

and diastereomers IIa and IIb are derived from general formula II,

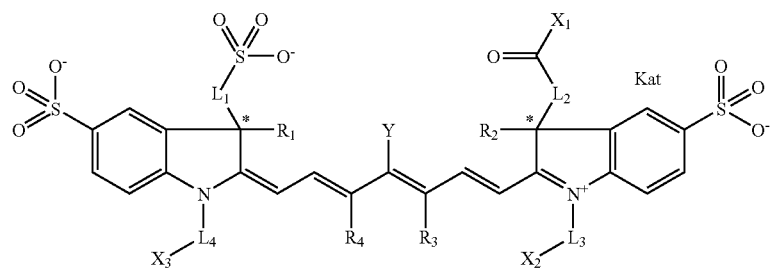

and whereby
- each of $R^1$ and $R^2$ is the same or different and is independently selected from the group consisting of an aliphatic and heteroaliphatic group;
- each of $L_1$ to $L_4$ is the same or different and is independently selected from the group consisting of a divalent linear ($—(CH_2)_o—$, o=1 to 15), crossed, or cyclic alkylene group which can be substituted by at least one atom selected from the group consisting of oxygen, substituted nitrogen, and sulfur;
- $X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-$CO_2$—NHS, —NR-L-$CO_2$—STP, —NR-L-$CO_2$-TFP, —NR-L-CO-benzotriazole, —NR-L-CHO, —NR-L-maleimid, and —NR-L-NH—CO—$CH_2$—I, R is —H or is equal to $R^1$ or $R^{2'}$ and L is equal to $L_1$ to $L_4$;
- each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof;
- Kat is a number of $Na^+$, $K^+$, $Ca^{2+}$, ammonia, or other cation(s) needed to compensate the negative charge brought by the cyanine;
- n in formula I is a integer from 0 to 3;

Y in formula II is selected from the group consisting of fluorine, chlorine, bromine, a substituted phenoxy-, and a substituted arylmercapto-(phenyl sulfanyl-) function; and each of $R^3$ and $R^4$ in formula II is the same or different and is independently an aliphatic or heteroaliphatic group respectively, or forms together the divalent structural element selected from the group consisting of —$(CH_2)_m$—, —$(CH_2)_mO(CH_2)_{m'}$—, —$(CH_2)_mS(CH_2)_{m'}$—, —$(CH_2)_mCH=CH$—, and —OCH=CH— where each of m and m' is the same or different and is a integer from 2 to 6.

6. The method of claim 5 wherein the diastereomer is conjugated to a biomolecule selected from at least one of a protein, antibody, enzyme, nucleoside triphosphate (NTP), oligonucleotide, biotin, hapten, cofactor, lectin, antibody binding protein, carotenoid, hormone, neurotransmitter, growth factors, toxin, biological cell, lipid, receptor binding drug, fluorescent proteins, organic polymer carrier material, or inorganic polymeric carrier material.

7. The method of claim 5 used in at least one of an immunoassay, hybridization, chromatographic assay, electrophoretic assay, microwell plate based assay, fluorescence resonance energy transfer (FRET) system, high throughput screening, or microarray.

8. The method of claim 5 wherein detection sensitivity is at least 0.1 ng.

9. The method of claim 5 wherein protein detection sensitivity is at least 0.1 pg protein.

* * * * *